US009469853B2

(12) United States Patent
Kolattukudy

(10) Patent No.: US 9,469,853 B2
(45) Date of Patent: Oct. 18, 2016

(54) MCPIP PROTECTION AGAINST OSTEOCLAST PRODUCTION

(71) Applicant: Pappachan Kolattukudy, Orlando, FL (US)

(72) Inventor: Pappachan Kolattukudy, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 81 days.

(21) Appl. No.: 14/194,254

(22) Filed: Feb. 28, 2014

(65) Prior Publication Data

US 2014/0302044 A1  Oct. 9, 2014
US 2016/0257960 A9  Sep. 8, 2016

Related U.S. Application Data

(63) Continuation of application No. 13/362,261, filed on Jan. 31, 2012, now abandoned, and a continuation of application No. 12/539,907, filed on Aug. 12, 2009, now abandoned, which is a continuation of application No. 11/643,057, filed on Dec. 20, 2006, now abandoned.

(60) Provisional application No. 60/826,428, filed on Sep. 21, 2006, provisional application No. 60/751,927, filed on Dec. 20, 2005.

(51) Int. Cl.
| C12N 15/11 | (2006.01) |
| C12N 15/113 | (2010.01) |
| A61K 31/713 | (2006.01) |
| A61K 35/28 | (2015.01) |
| C07K 16/18 | (2006.01) |

(52) U.S. Cl.
CPC ......... *C12N 15/1136* (2013.01); *A61K 31/713* (2013.01); *A61K 35/28* (2013.01); *C07K 16/18* (2013.01); *C12N 15/113* (2013.01); *C12N 2310/11* (2013.01); *C12N 2310/14* (2013.01)

(58) Field of Classification Search
CPC .......... C12N 15/1136; C12N 2310/11; A61K 35/28
See application file for complete search history.

(56) References Cited

U.S. PATENT DOCUMENTS

2007/0142288 A1*  6/2007  Kolattukudy et al. .......... 514/12
2009/0028876 A1*  1/2009  Teng ........................... 424/172.1

OTHER PUBLICATIONS

Mizgalska et al. (FEBS Journal 276, 2009, 7386-7399).*
Wang et al. (Mol. Cell Biol. 2011, 3, 360-368).*

Azfer A.,et al., "Activation of endoplasmic reticulum stress response during the development of ischemic heart disease." Am. J. Physiol. Heart Circ. Physiol., 2006; vol. 291: pp. H1411-H1420.
Baerga R., et al., "Targeted deletion of autophagy-related 5 (atg5) impairs adipogenesis in a cellular model and in mice." Autophagy, 2009; vol. 5: pp. 1118-1130.
Bedard K., et al., "The NOX family of ROS-generating NADPH oxidases: physiology and pathophysiology." Physiol. Rev., 2007; vol. 87: pp. 245-313.
Blommaart E.F., et al., "The phosphatidylinositol 3-kinase inhibitors wortmannin and LY294002 inhibit autophagy in isolated rat hepatocytes." Eur. J. Biochem., 1997; vol. 243: pp. 240-246.
Boyce B.F., et al., "New roles for osteoclasts in bone." Ann. NY Acad. Sci., 2007; vol. 1116: pp. 245-254.
Colosetti P.,et al., "Autophagy is an important event for megakaryocytic differentiation of the chronic myelogenous leukemia K562 cell line." Autophagy, 2009; vol. 5: pp. 1092-1098.
Decoursey T.E., et al., "Regulation and termination of NADPH oxidase activity." Cell. Mol. Life Sci., 2005; vol. 62: pp. 2173-2193.
Gersten R.E., et al., "A role of phosphoinositide 3-kinase in monocyte recruitment under flow conditions." J. Biol. Chem., 2001; vol. 276: pp. 26846-26851.
Glick D., et al., "Autophagy: cellular and molecular mechanisms." J. Pathol., 2010; vol. 221: pp. 3-12.
Goldman S., et al., "Autophagy and adipogenesis: implications in obesity and type II diabetes." Autophagy, 2010; vol. 6: pp. 179-181.
Ha J.,et al., "CXC chemokine ligand 2 induced by receptor activator of NF-kappa B ligand enhances osteoclastogenesis." J. Immunol., 2010; vol. 184: pp. 4717-4724.
Harris E.D. Jr., "Rheumatoid arthritis: pathophysiology and implications for therapy." N. Engl. J. Med., 1990; vol. 322: pp. 1277-1289.
Huang H., et al., "Osteoclast differentiation requires TAK1 and MKK6 for NFATc1 induction and NF-kappaB transactivation by RANKL." Cell Death Differ., 2006; vol. 13: pp. 1879-1891.
Kim M.S., et al., "MCP-1 is induced by receptor activator of nuclear factor-κB ligand, promotes human osteoclast fusion, and rescues granulocyte macrophage colony-stimulating factor suppression of osteoclast formation." J. Biol. Chem., 2005; vol. 280: pp. 16163-16169.
Kim M.S.,et al. "MCP-1-induced human osteoclast-like cells are tartrate-resistant acid phosphatase, NFATc1, and calcitonin receptor-positive but require receptor activator of NFkappaB ligand for bone resorption." J. Biol. Chem., 2006a; vol. 281: pp. 1274-1285.
Kim M.S., et al., "Induction of chemokines and chemokine receptors CCR2b and CCR4 in authentic human osteoclasts differentiated with RANKL and osteoclast like cells differentiated by MCP-1 and RANTES." J. Cell. Biochem., 2006b; vol. 97: pp. 512-518.
Kim D.S., et al., "p 38 mitogen-activated protein kinase is involved in endoplasmic reticulum stress-induced cell death and autophagy in human gingival fibroblasts." Biol. Pharm. Bull., 2008; vol. 33: pp. 545-549.

(Continued)

*Primary Examiner* — Brian Whiteman
(74) *Attorney, Agent, or Firm* — Timothy H. Van Dyke; Beusse, Wolter, Sanks & Maire, PLLC

(57) ABSTRACT

Disclosed herein are methods of treating a patient at risk of developing an inflammatory joint disease. In exemplary embodiments, the method involves inhibiting MCPIP levels in a patient in need, wherein said patient in need is exhibiting pre-arthritic or pre-osteoporotic symptoms.

20 Claims, 10 Drawing Sheets

(56) References Cited

OTHER PUBLICATIONS

Kim K.W., et al., "Endoplasmic reticulum stress mediates radiation-induced autophagy by perk-elF2alpha in caspase-3/7-deficient cells." Oncogene, 2010; vol. 29: pp. 3241-3251.
Kiviranta R.,et al., "Accelerated turnover of metaphyseal trabecular bone in mice overexpressing cathepsin K. J. Bone Miner." Res., 2001; vol. 16: pp. 1444-1452.
Leto T.L., et al., "Targeting and regulation of reactive oxygen species generation by Nox family NADPH oxidases." Antioxid. Redox Signal., 2009; vol. 11: pp. 2607-2619.
Liang J., et al., "A novel CCCH—zinc finger protein family regulates proinflammatory activation of macrophages." J. Biol. Chem., 2008; vol. 283: pp. 6337-6346.
Lu Y., et al. "Monocyte chemotactic protein-1 mediates prostate cancer-induced bone resorption." Cancer Res., 2007; vol. 67: pp. 3646-3653.
Malhotra J.D., et al., "Endoplasmic reticulum stress and oxidative stress: A vicious cycle or a double-edged sword?" Antioxid. Redox Signal., 2007; vol. 9: pp. 2277-2293.
Malhotra J.D.,et al., et al. "Antioxidants reduce endoplasmic reticulum stress and improve protein secretion." Proc. Natl Acad. Sci. USA, 2008; vol. 105: pp. 18525-18530.
Matsushita K., et al. "Zc3h12a is an RNase essential for controlling immune responses by regulating mRNA decay." Nature, 2009; vol. 458: pp. 1185-1190.
Miyamoto K., et al., "MCP-1 expressed by osteoclasts stimulates osteoclastogenesis in an autocrine/paracrine manner." Biochem. Biophys. Res. Commun., 2009; vol. 383: pp. 373-377.
Mundy G.R., "Osteoporosis and inflammation." Nutr. Rev., 2007; vol. 65: pp. S147-S151.
Niu J., et al., "Cardioprotective effects of cerium oxide nanoparticles in a transgenic murine model of cardiomyopathy." Cardiovasc. Res., 2007; vol. 73: pp. 549-559.
Niu J., et al., "Monocyte chemotactic protein (MCP)-1 promotes angiogenesis via a novel transcription factor, MCP-1-induced protein (MCPIP)." J. Biol. Chem., 2008; vol. 283: pp. 14542-14551.
Petiot A., et al., "Distinct classes of phosphatidylinositol 3'-kinases are involved in signaling pathways that control macroautophagy in HT-29 cells." J. Biol. Chem., 2000; vol. 275: pp. 992-998.
Sakaki K., et al., "R.J.Regulation of ER stress-induced macroautophagy by protein kinase" C. Autophagy, 2008; vol. 4: pp. 841-843.
Sakiyama H., et al., "Establishment and characterization of macrophage-like cell lines expressing osteoclast-specific markers." J. Bone Miner. Metab., 2001; vol. 19: pp. 220-227.
Sato K., et al., "Osteoclasts, rheumatoid arthritis, and osteoimmunology." Curr. Opin. Rheumatol., 2006; vol. 18: pp. 419-426.
Singh R., et al., "Autophagy regulates adipose mass and differentiation in mice." J. Clin. Invest., 2009; vol. 119: pp. 3329-3339.
Skalniak L., et al., "Regulatory feedback loop between NF-kappaB and MCP-1-induced protein 1 RNase." FEBS J., 2009; vol. 276: pp. 5892-5905.
Stappenbeck T.S., "The role of autophagy in Paneth cell differentiation and secretion.Mucosal." Immunol., 2010; vol. 3: pp. 8-10.
Steinbeck M.J., et al., "Trudeau M.J.Involvement of hydrogen peroxide in the differentiation of clonal HD-11EM cells into osteoclast-like cells." J. Cell. Physiol., 1998; vol. 176: pp. 574-587.

Sugimura R., et al., "Shifting in balance between osteogenesis and adipogenesis substantially influences hematopoiesis." J. Mol. Cell Biol., 2010; vol. 2: pp. 61-62.
Takami M., et al., "Ca2+-ATPase inhibitors and Ca2+-ionophore induce osteoclast-like cell formation in the cocultures of mouse bone marrow cells and calvarial cells." Biochem. Biophys. Res. Commun., 1997; vol. 237: pp. 111-115.
Tsai Y.Y., et al., "Novel synthesis of cerium oxide nanoparticles for free radical scavenging." Nanomedicine (Lond), 2007; vol. 2: pp. 325-332.
Vrotsos E.G., et al., "MCP-1 involvement in glial differentiation of neuroprogenitor cells through APP signaling." Brain Res. Bull., 2009; vol. 79: pp. 97-103.
Wang J.Beclin, "1 bridges autophagy, apoptosis and differentiation." Autophagy, 2008; vol. 4: pp. 947-948.
Wise G.E., et al., "R.N.Cellular, molecular, and genetic determinants of tooth eruption." Crit. Rev. Oral Biol. Med., 2002; vol. 13: pp. 323-334.
Wolf G., "Role of reactive oxygen species in angiotensin II-mediated renal growth, differentiation, and apoptosis." Antioxid. Redox Signal., 2005; vol. 7: pp. 1337-1345.
Xia C., et al., "Reactive oxygen species regulate angiogenesis and tumor growth through vascular endothelial growth factor." Cancer Res., 2007; vol. 67: pp. 10823-10830.
Xue X., et al., "Tumor necrosis factor alpha (TNFα) induces the unfolded protein response (UPR) in a reactive oxygen species (ROS)-dependent fashion, and the UPR counteracts ROS accumulation by TNFα." J. Biol. Chem, 2005; vol. 280: pp. 33917-33925.
Yamasaki N., et al., "High oxygen tension prolongs the survival of osteoclast precursors via macrophage colony-stimulating factor." Bone, 2009; vol. 44: pp. 71-79.
Yip K.H., et al., "Thapsigargin modulates osteoclastogenesis through the regulation of RANKL-induced signaling pathways and reactive oxygen species production." J. Bone Miner. Res., 2005; vol. 20: pp. 1462-1471.
Younce C.W., et al., "P.E.MCP-1 causes cardiomyoblast death via autophagy resulting from ER stress caused by oxidative stress generated by inducing a novel zinc-finger protein, MCPIP." Biochem. J., 2010; vol. 426: pp.43-53.
Younce C.W., et al., "P.E.MCP-1 (monocyte chemotactic protein-1)-induced protein, a recently identified zinc finger protein, induces adipogenesis in 3T3-L1 pre-adipocytes without peroxisome proliferator-activated receptor gamma." J. Biol. Chem., 2009; vol. 284: pp. 27620-27628.
Younce C.W., et al., "P.E.Hyperglycemia-induced cardiomyocyte death is mediated via MCP-1 production and induction of a novel zinc-finger protein MCPIP." Cardiovasc. Res., 2010; vol. 87: pp. 665-674.
Zeng M., et al., "Roles of autophagy and mTOR signaling in neuronal differentiation of mouse neuroblastoma cells." Cell. Signal., 2008; vol. 20: pp. 659-665.
Zhang K.H.,et al., "Ferritin heavy chain-mediated iron homeostasis and subsequent increased reactive oxygen species production are essential for epithelial-mesenchymal transition." Cancer Res., 2009; vol. 69: pp. 5340-5348.
Zhou L., et al., "Monocyte chemoattractant protein-1 induces a novel transcription factor that causes cardiac myocyte apoptosis and ventricular dysfunction." Circ. Res., 2006; vol. 98: pp. 1177-1185.

* cited by examiner

MCPIP PROTECTION AGAINST OSTEOCLAST PRODUCTION

CROSS REFERENCE TO RELATED APPLICATIONS

This application is a continuation of U.S. patent application Ser. No. 13/362,261, filed Jan. 31, 2012 now abandoned, and is a continuation of U.S. Ser. No. 12/539,907 filed Aug. 12, 2009, now abandoned, which is a Continuation of Ser. No. 11/643,057; filed Dec. 20, 2006, now abandoned, which claims benefit of U.S. Ser. No. 60/751,927 filed Dec. 20, 2005; all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 12, 2012, is named 10669150.txt and is 20,777 bytes in size.

BACKGROUND

There is strong evidence that osteoclast (OC) is the principal cell type responsible for bone resorption in inflammatory joint diseases (Harris, 1990; Sakiyama et al., 2001; Sato and Takayanagi, 2006; Mundy, 2007). Rheumatoid arthritis (RA) is characterized by the presence of inflammatory synovitis accompanied by the destruction of the joint cartilage and bone (Harris, 1990; Mundy, 2007; Sugimura and Li, 2010). OCs are bone-resorbing cells that differentiate from hematopoietic precursors of the monocyte/macrophage lineage (Sakiyama et al., 2001; Boyce et al., 2007). OCs are multinuclear giant cells that stain positive for tartrate-resistant acid phosphatase (TRAP) and serine protease cathepsin K (CTSK) (Kiviranta et al., 2001; Boyce et al., 2007).

Monocyte chemotactic protein-1 (MCP-1), a CC chemokine commonly found at the site of tooth eruption, RA bone degradation, and bacterially induced bone loss (Wise et al., 2002), is known to induce differentiation of monocytes into TRAP and CTSK-positive precursors of OCs. MCP-1 is expressed by mature OCs and its expression is regulated by nuclear factor-κB (NF-κB) (Kim et al., 2005). Several reports showed that MCP-1 is induced by NF-κB ligand RANKL and promotes OC fusion into multinuclear TRAP-positive cells without bone-resorption activity (Kim et al., 2006a,b), which might be called OC precursors. Recently, it has been reported that MCP-1 plays an important role in regulating OC differentiation in an autocrine/paracrine manner under stimulation by RANKL (Miyamoto et al., 2009). How MCP-1 mediates OC differentiation remains unclear.

The cellular effect of MCP-1 is mediated by the CCR2, a G-protein-coupled receptor that is induced by the receptor activator of RANKL (Gerszten et al., 2001; Kim et al., 2005). The signaling process initiated by MCP-1 binding to CCR2 leads to changes in gene expression.

Recently, it was found that this MCP-1 binding leads to the induction of a novel zinc-finger protein called MCPIP in human peripheral blood monocytes (Zhou et al., 2006). The biological functions of MCPIP, however, remain poorly understood.

SUMMARY

The importance of the way in which MCP-1 mediates OC differentiation has been realized, which has been heretofore unclear. The role of MCPIP in biological processes initiated by MCP-1 has also now been discovered. It was previously understood that MCPIP mediates several biological processes initiated by MCP-1. including cardiomyocyte death (Younce and Kolattukudy, 2010; Younce et al., 2010), adipogenesis (Younce et al., 2009), angiogenesis (Niu et al., 2008), and glial differentiation of neuroprogenitor cells (Vrotsos et al., 2009). It has been discovered, as disclosed herein, that MCP-1 induces differentiation of monocytic cells into OC precursors via MCPIP. It is therefore presented that MCPIP mediates differentiation of OC precursors via induction of oxidative stress that causes endoplasmic reticulum (ER) stress that leads to autophagy involved in osteoclastogenesis. These findings implicate that MCPIP is a novel factor involved in OC precursor differentiation, and thus it serves as a new target for diagnosis and treatment of osteoporosis-related disease.

DETAILED DESCRIPTION

Figure 1:
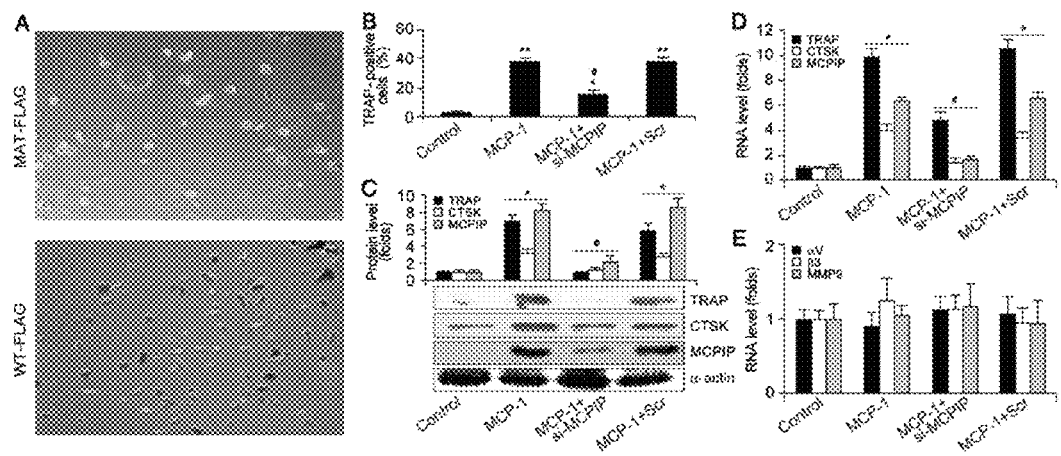
FIG. 1. MCP-1 induction of OC precursor differentiation, mediated by MCPIP. (A and B) BMCs were transfected with FLAG-tagged MCPIP (WT-MCPIP) or FLAG-tagged empty vector (MAT-FLAG). TRAP-expressing cells were stained and viewed under the Nikon microscope (A). BMNCs treated with MCP-1 alone or with MCPIP siRNA or Scr siRNA. TRAP-expressing cells were stained and TRAP-positive cell proportion was measured (B). At least three fields (~500 cells), were chosen. *$P<0.05$ and **$P<0.01$ versus control; #$P<0.05$ versus Scr. (C) Immunoblotting showing the expression of TRAP, CTSK, and MCPIP induced by MCP-1. Data were mean±SD (n=3). *$P<0.05$ versus control; #$P<0.05$ versus Scr. (D) Real-time PCR showing the transcription of TRAP, CTSK, and MCPIP induced by MCP-1. *$P<0.05$ versus control; #$P<0.05$ versus Scr. (E) Real-time PCR showing the transcription of αV integrin, β3 integrin, and MMP9.

The inventors previously identified the novel transcription factor designated as MCPIP (MCP-1-induced protein). MCPIP was initially isolated from human monocytes after stimulation with MCP-1. The nucleotide (SEQ ID NO: 1) and amino acid (SEQ ID NO: 2) sequences of isolated human MCPIP were deposited with GenBank under accession number AY920403 and the nucleotide (SEQ ID NO: 3) and amino acid (SEQ ID NO: 4) sequences of isolated mouse MCPIP were deposited with GenBank under accession number AY920404.

The inventors have continued to study the biological relevance of these genes/proteins, and to develop new therapies based on this research. This invention is based on the discovery that MCP-1 induces MCPIP in human peripheral blood monocytes which induces differentiation of monocytes into osteoclast cells (OC) or OC precursors. $NF_KB$ is a master controller of inflammation in the body. Agonists of MCPIP would enhance its anti-inflammatory potentcy; it is herein discovered that inhibition of the activation of $NF_KB$ by MCPIP provides a significant potential as an anti-inflammatory agent. Therefore, inhibition of the activation of $NF_KB$ by inhibiting MCPIP has a significant use as an anti-inflammatory agent. Inhibition of MCPIP inhibits inflammation, which plays a critical role in diseases including angiogenesis, i.e., the physiological process involving the growth of new blood vessels from pre-existing vessels, adipogenesis, the process of cell differentiation by which preadipocytes become adipocytes, and osteoclastogenesis, i.e., the development of osteoclasts. Furthermore, MCPIP plays a critical role in the differentiation of osteoclasts involved in inflammatory bone loss that occurs in many inflammatory diseases such as, for example, rheumatoid arthritis. Additionally, elevated MCP-1 levels have been identified as a direct cause of insulin resistance. MCPIP has been discovered to mediate insulin resistance, and thus, MCPIP inhibitors enhance insulin sensitivity. Additional research has led to the identification of MCPIP as a novel factor involved in OC precursor differentiation, as provided herein, identifies MCPIP as a new target for diagnosis and treatment of osteoporosis-related disease.

Discovered herein is the effect of inhibition of MCPIP in reducing osteoclast precursor differentiation. MCPIP plays a critical role in differentiation of osteoclasts involved in inflammatory bone loss that occurs in many inflammatory diseases such as rheumatoid arthritis. It is disclosed herein that differentiation of monocytes to OC precursors is mediated by MCPIP. Therefore, the blocking or inhibition of MCPIP provides a promising therapeutic strategy for preventing differentiation of monocytes to OC precursors, and ultimately the prevention of bone resorption. Bone resorption is a process by which osteoclasts break down bone and release minerals, resulting in a transfer of calcium from bone fluid to the blood. This discovery provides a particular benefit in inflammatory joint diseases.

Ultimately, inflammatory bone erosion is involved in many pathological conditions (Lu et al., 2007; Ha et al., 2010). The novel inventive features described and contemplated herein provide a new insight into the mechanism by which MCP-1 induces differentiation of monocytic cells into TRAP- and CTSK-expressing cells that can proceed to differentiate into functional OCs in the presence of RANKL, and demonstrate that MCPIP is a novel target for therapy of inflammatory bone erosion, in one exemplary embodiment.

According to one embodiment of the invention, a method of treating a condition in a patient in need includes administering to the patient a therapeutically effective amount of a composition that inhibits the expression or action of MCPIP. The patient in need may be exhibiting pre-arthritic symptoms including but not limited to pain or tenderness in a joint which is aggravated by movement or activity, inflammation indicated by joint swelling, stiffness, redness, and/or warmth, joint deformity, loss of range of motion or flexibility in a joint, or unexplained weight loss. Additional pre-arthritic symptoms include extreme fatigue, lack of energy, weakness or a feeling of malaise, a non-specific fever, or crepitus, i.e., creaky, popping or snapping joints.

In another embodiment, the patient in need may be exhibiting pre-osteoporotic symptoms, including but not limited to back pain caused by a fractured or collapsed vertebra, loss of height over time, a stooped posture, or a bone fracture that occurs much more easily than expected. The patient in need may also be exhibiting symptoms of an existing arthritic or osteoporotic disease, or both. Furthermore, the patient in need may be exhibiting symptoms of any arthritic or osteoporotic related-diseases, any inflammatory joint diseases, or any pre-disease symptoms of these related diseases. In a further embodiment, the condition may include an osteoporosis-related condition, and in a particular embodiment, rheumatoid arthritis.

As used herein, therapeutically effective amount refers to an amount sufficient to elicit the desired biological response. In the present invention the desired biological response can be an overall improvement in the condition being treated. The overall improvement can be associated with improvement in individual symptoms.

Subject or patient, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In one embodiment, the subject is a human.

Modes of Administration

The compounds for use in the method of the invention can be formulated for oral, transdermal, sublingual, buccal, parenteral, rectal, intranasal, intrabronchial, intrapulmonary, or ocular administration. Oral administration is preferred. For oral administration, the compounds can be of the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets can be coated using suitable methods and coating materials such as OPADRY film coating systems available from Colorcon, West Point, Pa. (e.g., OPADRY, OY Type, OY-C Type, Organic Enteric OY-P Type, Aqueous Enteric OY-A Type, OY-PM Type and OPADRY® White, 32K18400).

In a particular embodiment, the oral form is a tablet containing MCPIP and a pharmaceutically acceptable excipient, such as, but not limited to mannitol, corn starch, microcrystalline cellulose, colloidal silicon dioxide, polyvinyl pyrrolidone, talc, magnesium stearate, and the like which are optionally coated with an OPADRY film coating.

Liquid preparation for oral administration can be in the form of solutions, syrups or suspensions. The liquid preparations can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

For buccal administration, the compounds for use in the method of the invention can be in the form of tablets or lozenges formulated in a conventional manner.

For parenteral administration, the compounds for use in the method of the invention can be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

For rectal administration, the compounds for use in the method of the invention can be in the form of suppositories or enemas. For sublingual administration, tablets can be formulated in conventional manner.

For intranasal, intrabronchial or intrapulmonary administration, conventional formulations can be employed.

Further, the compounds (e.g. protein or delivery vehicle) for use in the method of the invention can be formulated in a sustained release preparation. For example, the compounds can be formulated with a suitable polymer or hydrophobic material which provides sustained and/or controlled release properties to the active agent compound. As such, the compounds for use the method of the invention can be administered in the form of microparticles for example, by injection or in the form of wafers or discs by implantation.

In accordance with the method of the invention, an expression vector is a viral or a non-viral expression vector. Viral expression vectors which may be used advantageously in the method of the invention include, but are not limited to, an adeno associated virus (AAV) vector, a lentivirus vector, an adenovirus vector, and a herpes simplex virus (HSV) vector.

In additional embodiments, the composition comprises siRNA or miRNA specific for MCPIP, an antisense nucleotide specific for MCPIP, and/or shRNA. In an alternative embodiment, the composition comprises an antibody specific to MCPIP.

In another embodiment, a method of inhibiting osteoclast production (or a method of reducing osteoclast precursor cells) in a patient in need is provided. The method includes administering a therapeutically effective amount of a composition that inhibits the expression or action of MCPIP in the patient. The patient in need, in an embodiment, may be exhibiting symptoms of rheumatoid arthritis, osteoarthritis, and/or osteoporosis.

In another embodiment, administering a therapeutically effective amount of a composition includes a composition comprising: a composition that inhibits the expression or action of MCPIP, and a pharmaceutically acceptable excipient.

In further embodiments, the composition includes an MCPIP siRNA, an shRNA, an antibody specific to MCPIP, and/or an antisense nucleotide specific for MCPIP.

Many of the embodiments of the subject invention make reference to particular methods of inhibiting expression. The subject invention is not to be limited to any of the particular methods described. One such method includes siRNA (small interfering/short interfering/silencing RNA). SiRNA most often is involved in the RNA interference pathway where it interferes with the expression of a specific gene. In addition to its role in the RNA interference pathway, siRNA also act in RNA interference-related pathways, e.g., as an antiviral mechanism or in shaping the chromatin structure of a genome.

Another method by which to inhibit expression and to inhibit the expression of MCPIP in particular is shRNA. ShRNA (short hairpin or small hairpin RNA) refers to a sequence of RNA that makes a tight hairpin turn and is used to silence gene expression via RNA interference. It uses a vector introduced into cells and a U6 or H1 promoter to ensure that the shRNA is always expressed. The shRNA hairpin structure is cleaved by cellular machinery into siRNA which is then bound to the RNA-induced silencing complex. This complex binds to and cleaves mRNAs which match the siRNA that is bound to it.

MCPIP can also be blocked by subjecting procured cells to an antibody specific to MCP-1. An antisense nucleotide may also be used to block or inhibit expression, in particular, the expression of MCP-1. Expression may also be inhibited with the use of a morpholino oligomer or phosphorodiamidate morpholino oligomer (PMO). PMOs are an antisense technology used to block access of other molecules to specific sequences within nucleic acid. PMOs are often used as a research tool for reverse genetics, and function by knocking down gene function. This is achieved by preventing cells from making a targeted protein or by modifying splicing of pre-mRNA.

EXAMPLES

Example 1

MCP-1 Induces OC-Related Gene Expression Via MCPIP in Human Bone Marrow Monocytes It has been demonstrated that MCP-1 induces TRAP-positive OC precursor formation from human peripheral blood mononuclear cells (Kim et al., 2006a). Here, we found that 50 ng/ml MCP-1 induced TRAP-positive OC precursor cell formation from human bone marrow mononuclear cells (BMCs) (FIG. 1B). Immunoblotting (FIG. 1C) and real-time polymerase chain reaction (PCR) (FIG. 1D) showed that MCP-1 treatment induced expression of OC markers TRAP and CTSK. However, MCP-1 did not affect the expression of the OC functional markers αV integrin, β3 integrin, and MMP9 (FIG. 1E). We also found that 50 ng/ml MCP-1 induced up-regulation of MCPIP protein and mRNA levels, which can be suppressed by treatment with MCPIP small interfering RNA (siRNA) (FIGS. 1C and D). Compared with FLAG-tagged empty vector (MAT-FLAG), expression of FLAG-tagged MCPIP (WT-FLAG) induced TRAP-positive OC precursor cell formation (FIG. 1A). MCPIP siRNA also significantly inhibited the formation of OC precursor cells that expressed TRAP and CTSK but showed no effects on expression of αV integrin, β3 integrin, and MMP9 (FIG. 1C-E). These results suggest that induction of the TRAP-positive OC precursor cells by MCP-1 treatment of BMCs was mediated via MCPIP.

Example 2

Figure 2:
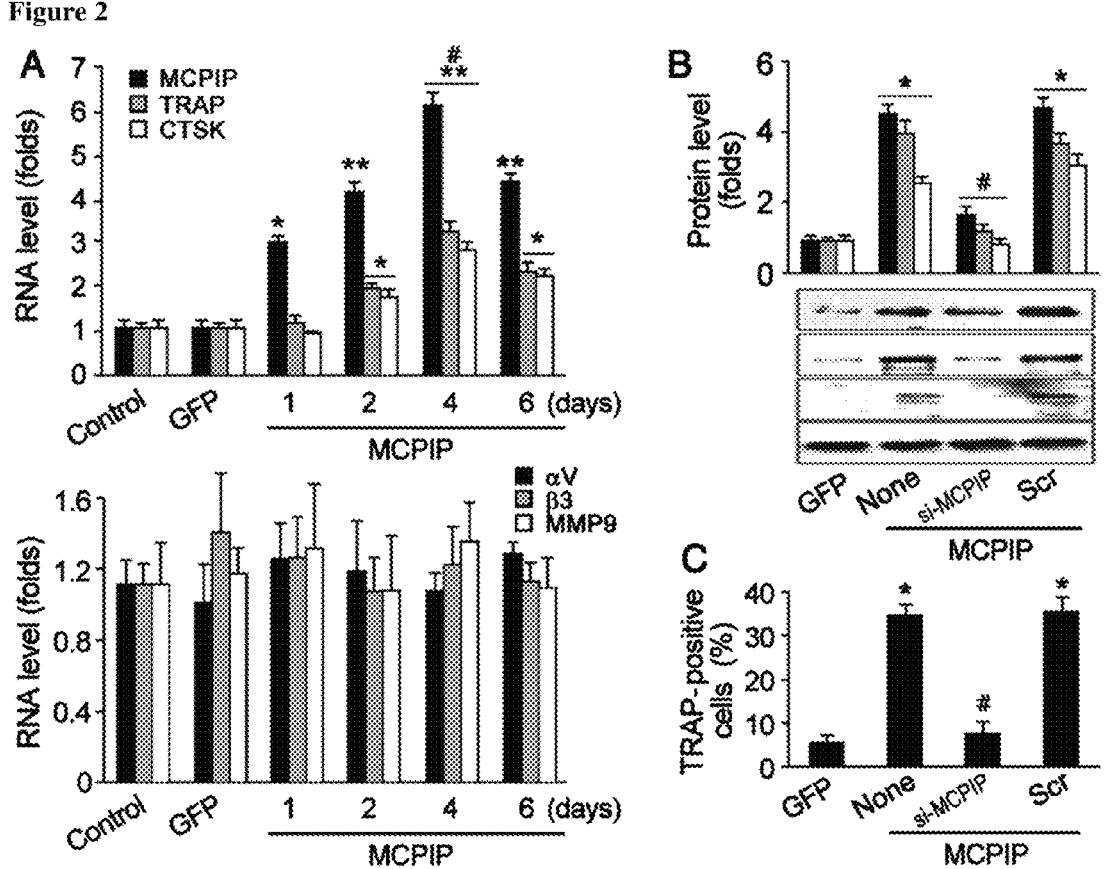
FIG. 2. MCPIP overexpression induces OC-related marker TRAP and CTSK expression. (A) Real-time PCR showing the transcription of TRAP, CTSK, and MCPIP (upper panel) and αV integrin, β3 integrin, and MMP9 (lower panel) induced by MCPIP transfection. *$P<0.05$ and **$P<0.01$ versus control or GFP; #$P<0.05$ versus day 2 or 6. (B) Immunoblotting showing the expression of TRAP, CTSK, and MCPIP induced by MCPIP transfection. Data were mean±SD (n=3). *$P<0.01$ versus GFP; #$P<0.05$ versus MCPIP or Scr. (C) Percentage of TRAP-positive cells. *$P<0.01$ versus GFP; #$P<0.01$ versus none or Scr.

Forced Expression of MCPIP Induces Differentiation of Monocytes into OC Precursors If MCP-1-induced differentiation of OC precursors is mediated by MCPIP, forced expression of MCPIP in monocytes might be expected to induce the formation of TRAP-positive OC precursor cells without MCP-1. BMCs were transfected to test this concept, as can be seen in FIG. 2, with MCPIP-GFP expression vector. Increased expression of MCPIP was found 24 h after transfection at mRNA levels as measured by real-time PCR and its expression reached the peak at 4 days after transfection (see FIG. 2A, upper panel). The expression of TRAP and CTSK was induced at 2 days after MCPIP transfection and reached the peak at 4 days. However, the expression of αV integrin, β3 integrin, and MMP9 showed no significant changes after MCPIP transfection (see FIG. 2A, bottom panel). Immunoblot analysis showed that MCPIP overexpression induced expression of TRAP and CTSK (see FIG. 2B), and TRAP staining showed that MCPIP expression significantly elevated formation of TRAP-positive cells (FIG. 2C). When MCPIP siRNA was transfected into BMCs for 24 h prior to MCPIP transfection, MCPIP expression was knocked down and the expression of OC-related genes TRAP and CTSK also were down-regulated (FIG. 2B). Moreover, the percentage of TRAP-positive cells was lowered by treatment with MCPIP siRNA (FIG. 2C). These results suggest that MCPIP transfection causes induction of OC-related genes and formation of TRAP-positive OC precursor cells.

Example 3

Figure 3:
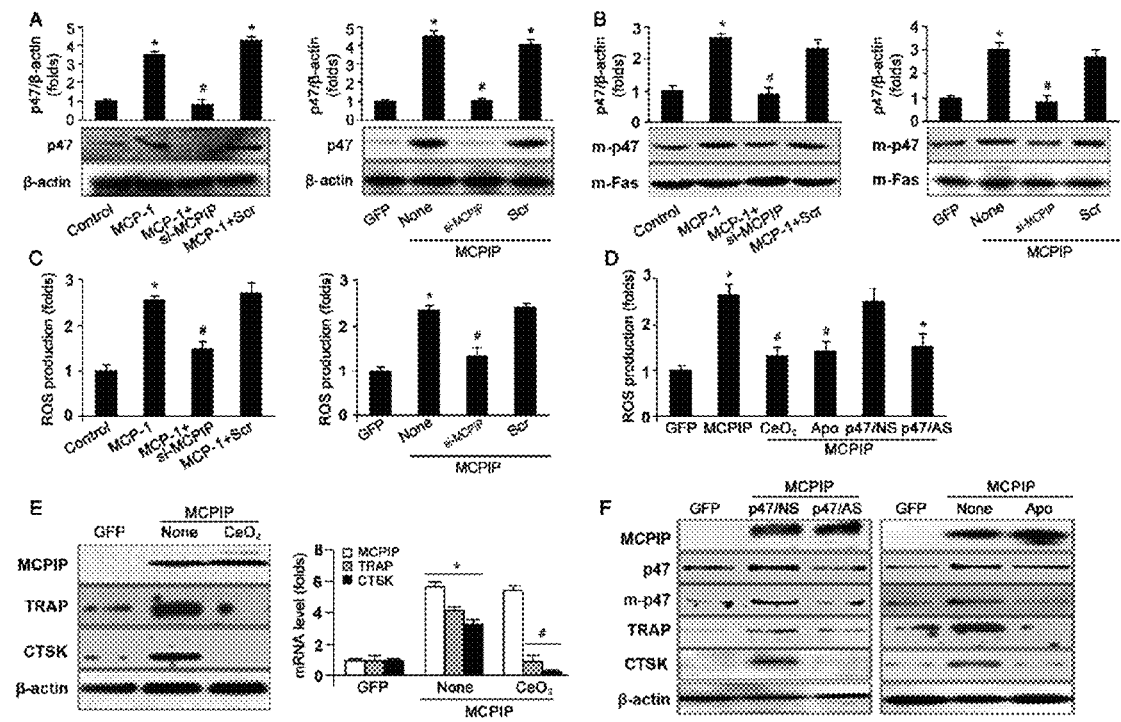
FIG. 3. ROS production involvement in MCPIP/MCP-1-induced OC precursor differentiation. (A) Western blot showed that MCP-1 treatment or MCPIP transfection induces $p47^{PHOX}$ expression. *$P<0.05$ versus control or GFP; #$P<0.05$ versus Scr. (B) Immunoblotting showed that MCP-1 or MCPIP overexpression induces an increase in cytoplasmic membrane-associated $p47^{PHOX}$. *$P<0.05$ versus control or GFP; #$P<0.05$ versus Scr. (C) ROS production induced by MCP-1 or MCPIP transfection, or siRNA was detected by using DHR123. *$P<0.05$ versus control or GFP; #$P<0.05$ versus Scr. (D) MCPIP-induced ROS production was inhibited by ROS, NAD(P)H oxidase inhibitors, and $p47^{PHOX}$ knockdown. *$P<0.05$ versus GFP, #$P<0.05$ versus MCPIP only. *$P<0.05$ compared with $p47^{PHOX}$ non-specific (NS) oligonucleotides transfection cells. (E) The effect of $CeO_2$ on MCPIP, TRAP, and CTSK expression induced by MCPIP transfection. Data were mean±SD (n=3). *$P<0.05$ versus GFP; #$P<0.05$ versus MCPIP only. (F) The effect of $p47^{PHOX}$ AS and apocynin on the expression of related proteins. m-p47, membrane located p47$^{PHOX}$; p47, total p47$^{PHOX}$; p47/NS, non-specific RNA; p47/AS, antisense RNA. Apo, apocynin.
Figure 7:
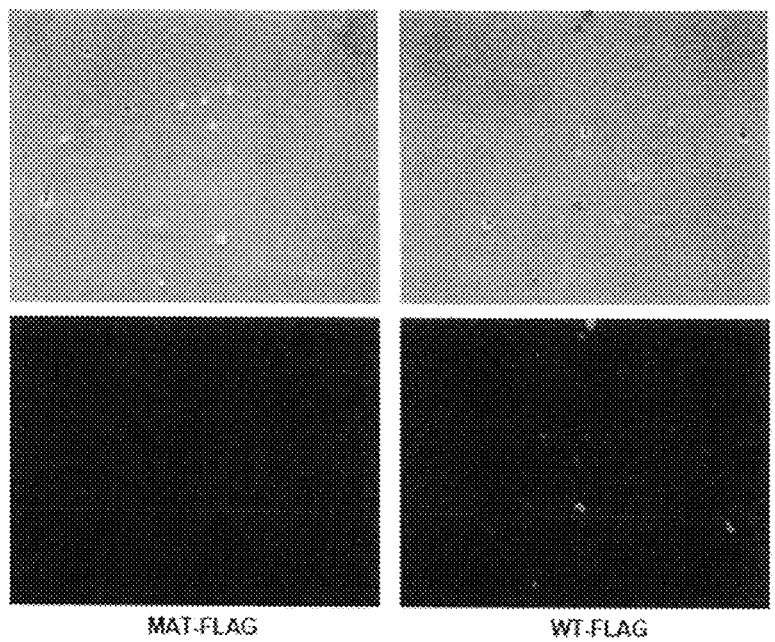
FIG. 7. MCPIP induced production of cellular ROS in bone marrow mononuclear cells (BBMN). Cells were transfected with empty vector (MAT-FLAG) orMCPIP-expression vector (WT-MCPIP) and after 24 hr stained with DHR123 that is a cell permeable nonfluorescent reagent that generates a fluorescent product (red) when oxidized by cellular ROS.

MCPIP-Induced Reactive Oxygen Species Production is Involved in OC Precursor Differentiation Reactive oxygen species (ROS) derived from NADPH oxidase have been suggested to regulate OC differentiation and prolong the survival of OC precursors (Yamasaki et al., 2009). p47PHOX, a regulatory subunit of NADPH oxidase, has been implicated in ROS generation (Decoursey and Ligeti, 2005). Herein, it was tested whether forced expression of MCPIP could induce expression and activation of NADPH oxidase by translocation of p47PHOX into the membrane and produce ROS. Dihydrorhodamine 123 (DHR123) staining revealed ROS production by MCPIP transfected cells but not MAT-FLAG controls (FIG. 7). Immunoblot analysis shows that MCP-1 treatment and MCPIP expression increased the expression of p47PHOX (FIG. 3A) and its translocation from the cytoplasm into the membrane (FIG. 3B). ROS production caused by MCP-1 treatment and MCPIP expression was assessed by DHR123 staining and results showed that MCP-1 treatment and MCPIP transfection remarkably increased ROS generation. Moreover, the effects of MCP-1 treatment or forced MCPIP expression on the expression and translocation of p47PHOX and ROS generation were inhibited by MCPIP siRNA (FIG. 3A-C).

Figure 8:
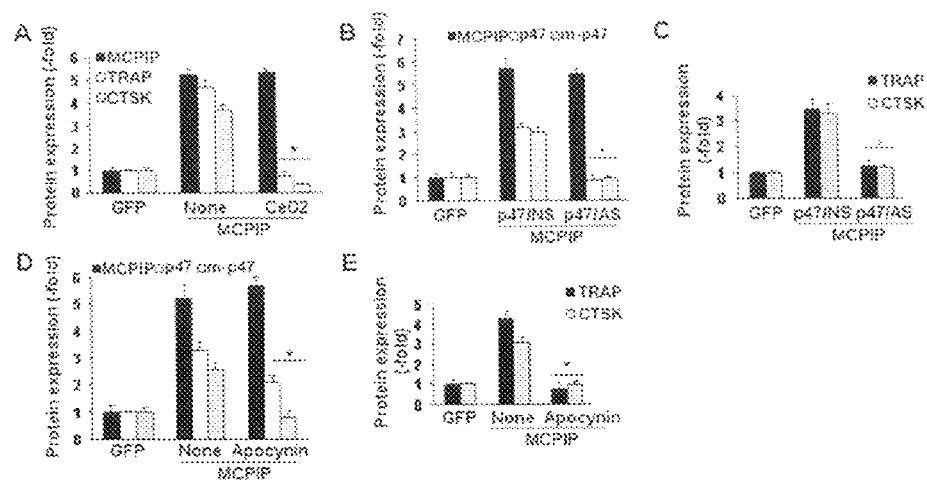
FIG. 8. ROS production involvement in MCPIP/MCP-1 induced OC precursor differentiation. Bone marrow monocytes were pretreated with CeO2 or apocynin for 6 h or p47PHOXantisense oligonucleotides for 24 h and then cells were transfected with MCPIP or GFP for 4 days. Cell lysate was collected and analysed using immunoblot with appropriate antibody and results were quantified against β-actin. A, Effect of CeO2 on MCPIP-induced TRAP and CTSK expression [*P<0.05 compared to CeO2-untreated cells ("None")]. B, Effect of p47 PHOX antisense oligonucleotides on expression of p47 PHOX and its translocation from cytoplasm to membrane [*P<0.05 compared to nonsense oligonucleotides treated cells ("p47/NS")]. C, Effect of p47 PHOX antisense oligonucleotides on MCPIP-induced TRAP and CTSK expression [*P<0.05 compared to non-sense oligonucleotides treated cells ("p47/NS")]. D, Effect of apocynin on expression of p47PHOX and its translocation from cytoplasm to membrane [*P<0.05 compared to apocynin-untreated cells ("None")]. E, Effect of apocynin on MCPIPinduced TRAP and CTSK expression [*P<0.05 compared to apoicynin-untreated cells ("None")].

To understand the involvement of ROS production in MCPIP-mediated formation of TRAP-positive OC precursor cells, BMCs were treated with $CeO_2$ nanoparticles, an inhibitor of ROS (Tsai et al., 2007) prior to MCPIP transfection. It was found that MCPIP-induced ROS production was significantly inhibited by $CeO_2$ (FIG. 3D). Immunoblot and real-time PCR analysis showed that $CeO_2$ inhibited MCPIP-induced TRAP and CTSK expression both at protein and mRNA levels (FIG. 3E and FIG. 8A). The effect of apocynin, an inhibitor of NADPH oxidase on MCPIP-induced induction of OC-related genes TRAP and CTSK was further tested herein. It was found that apocynin suppressed MCPIP-induced ROS production (FIG. 3D) and expression of TRAP and CTSK (FIG. 3F and FIG. 8E). Moreover, apocynin inhibited MCPIP-induced expression and membrane translocation of $p47^{PHOX}$ (FIG. 3F and FIG. 8D). Furthermore, knock-down of $p47^{PHOX}$ by its specific antisense oligonucleotides (p47/AS) also decreased ROS production, expression and translocation of $p47^{PHOX}$, and expression of OC-related genes TRAP and CTSK (FIG. 3F and FIGS. 8B and C). These results suggest that MCPIP causes ROS production by up-regulating $p47^{PHOX}$ expression and its membrane translocation, and that ROS generation is involved in MCP-1-induced OC precursor differentiation.

Example 4

Figure 4:
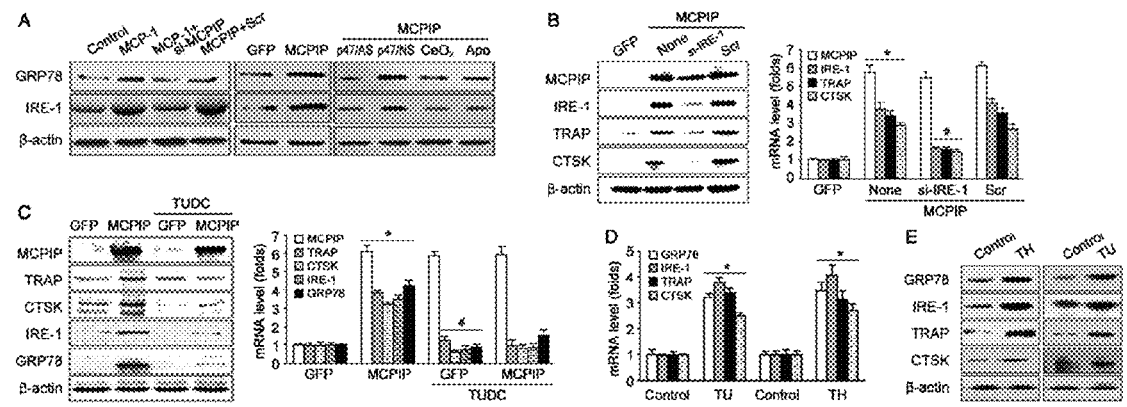
FIG. 4. MCPIP induction of ER stress via ROS production involved in OC precursor differentiation. (A) Immunoblotting shown that MCP-1 or MCPIP transfection induces the expression of GRP78 and IRE-1 (ER stress markers) by inducing ROS production. (B) Blockage of ER stress by IRE-1 siRNA abolished MCPIP-induced mRNA and protein expression of TRAP and CTSK. *P<0.05 versus GFP, #P<0.05 versus Scr. (C) Blockage of ER stress by TUDC abolished MCPIP-induced mRNA and protein expression of TRAP and CTSK. *P<0.05 versus GFP, #P<0.05 versus MCPIP alone. (D) Real-time PCR showing the expression of TRAP, CTSK, GRP78, and IRE-1 by ER stress inducer. *P<0.05 versus control. (E) Immunoblotting showing the expression of TRAP, CTSK, GRP78, and IRE-1 by ER stress inducer. TU, tunicamycin; TH, thapsigargin.
Figure 9:
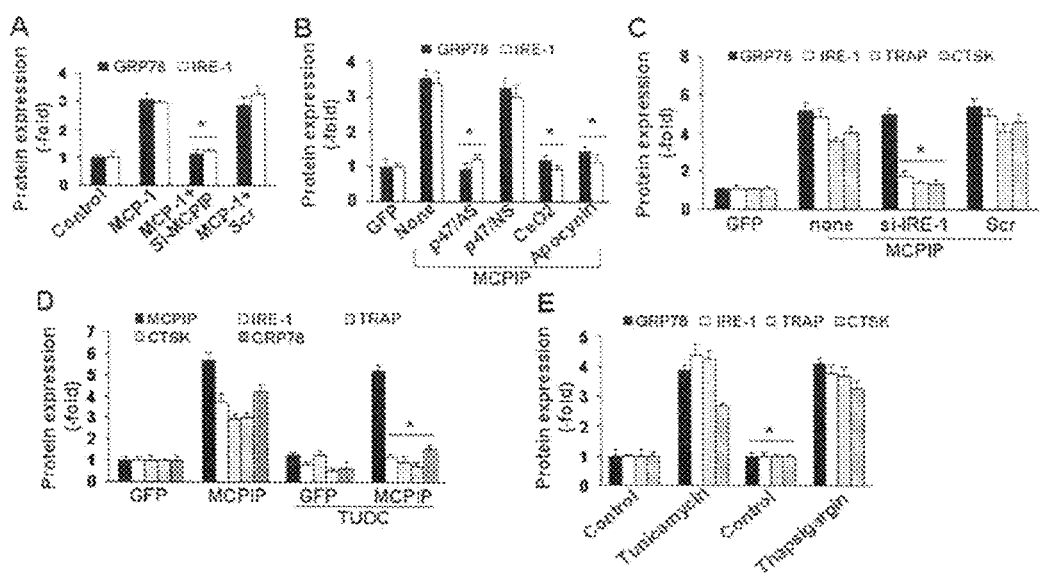
FIG. 9. MCPIP induces ER stress via ROS production which involvement in OC precursor differentiation. After treatment, cell lysate was collected and analysed using immunoblot with appropriate antibody and results were quantified against β-actin. A, MCP-1 induces ER stress marker GRP78 and IRE-1 expression via MCPIP (*P<0.05). B, Effect of p47PHOX antisense oligonucleotides, Ce02 and apocynin on MCPIP-induced expression of GRP78 and IRE-1 (*P<0.05). C, inhibition of ER stress by using knockdown of IRE-1 attenuates MCPIP-induced expression of TRAP and CTSK (*P<0.05). D, pretreatment of TUDC inhibits MCPIP-induced expression of TRAP and CTSK and ER stress marker IRE-1 and GRP78 (* P<0.05). E, ER stress inducer tunicamycin and thapsigargin induce expression of TRAP and CTSK (*P<0.05).

MCPIP-Induced ROS Production Causes an ER Stress Response that is Involved in OC Precursor Differentiation It has been reported that oxidative stress can induce ER stress (Xue et al., 2005; Malhotra et al., 2008). Therefore, it was tested herein whether MCP-1 treatment induces ER stress in BMCs. Immunoblot analysis showed that MCP-1 treatment induced expression of the ER stress markers 78 kDa glucose regulated protein (GRP78) and inositol-requiring enzyme-1 (IRE-1) (FIG. 4A, left panel, and FIG. 9A). This induction was inhibited by MCPIP siRNA (FIG. 4A, left panel, and FIG. 9A), indicating that MCP-1 induced ER stress via MCPIP. It was also found that forced expression of MCPIP induced ER stress with up-regulation of GRP78 and IRE-1 as indicated by immunoblot (FIG. 4A and FIG. 9B). To test whether MCPIP induces ER stress through oxidative stress, ROS production was suppressed by $CeO_2$, apocynin, and p47/AS, and then immunoblotting was performed. Results showed that MCPIP-induced expression of GRP78 and IRE-1 was attenuated by $CeO_2$, apocynin, and p47/AS (FIG. 4A and FIG. 9B). These results suggest that MCP-1 mediated ER stress via MCPIP-induced ROS production.

To understand whether ER stress is involved in MCPIP-induced expression of OC-related genes TRAP and CTSK, MCPIP-induced ER stress was inhibited by IRE-1 siRNA (FIG. 4B and FIG. 9C) and the ER stress-specific inhibitor tauroursodeoxycholate (TUDC) (FIG. 4C and FIG. 9D). Immunoblot and real-time PCR analysis showed that MCPIP-induced expression of TRAP and CTSK was significantly inhibited by IRE-1 siRNA and by TUDC at both protein and mRNA levels but did not affect the expression of MCPIP (FIGS. 4B and C).

If ER stress is critically important for OC differentiation, the inventors identified that ER stress inducers might induce differentiation of OC precursors without other inducers. In fact, two ER stress inducers, tunicamycin (TU) and thapsigargin (TH), induced expression of GRP78, IRE-1, TRAP, and CTSK at both protein and mRNA levels (FIGS. 4D and E and FIG. 9E). This result discovered by the inventors suggests that induction of ER stress alone could induce OC precursor differentiation. These results strongly support the conclusion that MCPIP-induced ER stress is involved in MCP-1-mediated OC precursor differentiation.

Example 5

Figure 5:
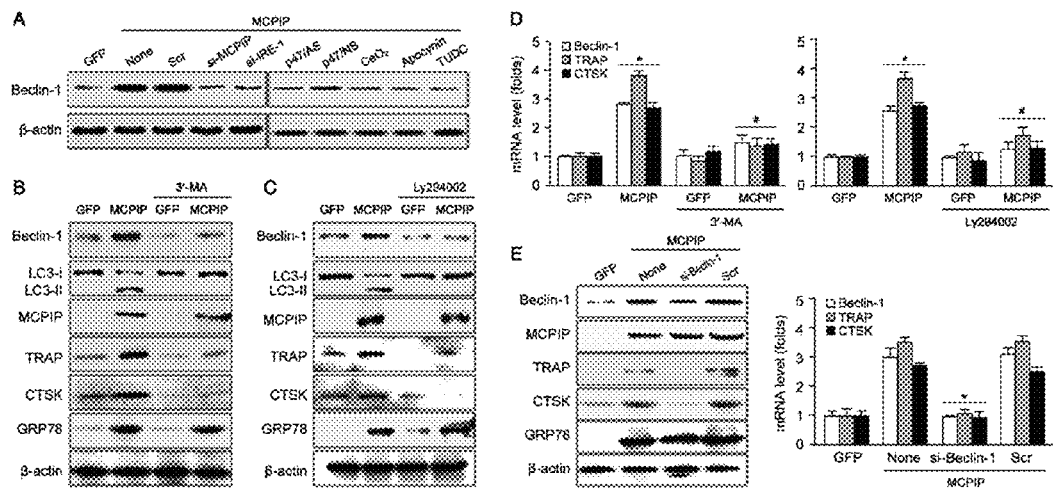
FIG. 5. MCPIP induction of autophagy via ROS production and ER stress involved in OC precursor differentiation. (A) Immunoblotting shown that MCPIP induces autophagy characterized with the marker Beclin-1 expression and ROS/ER stress inhibitor inhibited MCPIP-induced expression of Beclin-1. (B and C) Immunoblotting shown that autophagy blocker 3'-MA and LY294002 blocked MCPIP-induced OC-related gene TRAP and CTSK expression but not GRP78. (D) Real-time PCR shown that autophagy blocker 3'-MA and LY294002 blocked MCPIP-induced expression of TRAP and CTSK but not GRP78. *P<0.05 versus GFP, #P<0.05 versus MCPIP alone. (E) Blocking autophagy by Beclin-1 siRNA inhibited MCPIP-induced mRNA and protein expression of TRAP and CTSK but not GRP78. *P<0.05 versus MCPIP alone.
Figure 10:
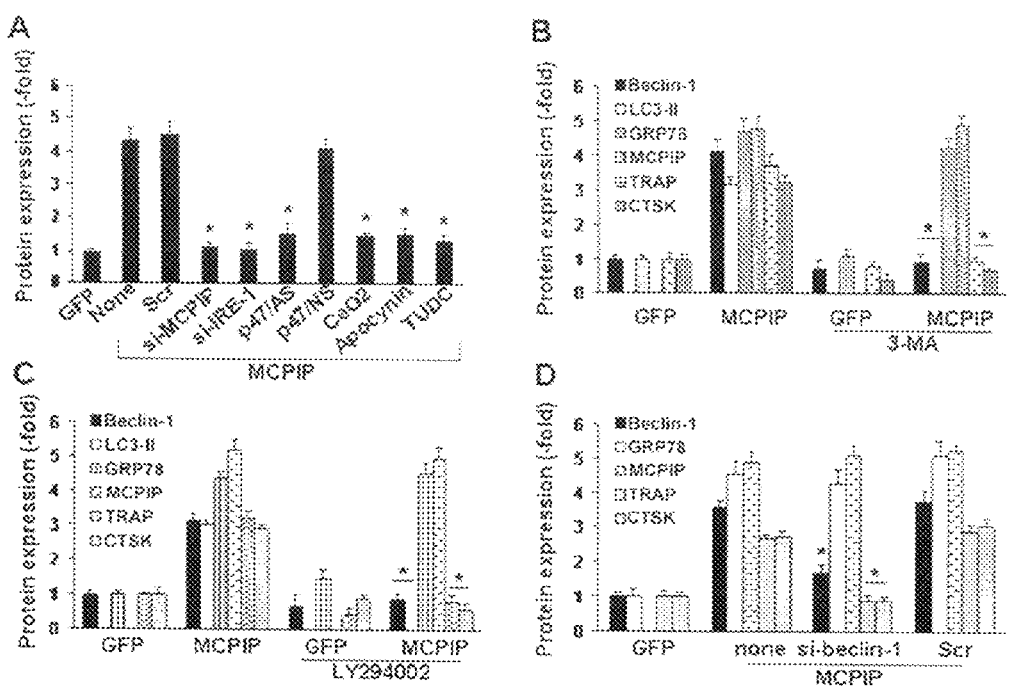
FIG. 10. MCPIP induces autophagy via ROS production and ER stress which involvement in OC precursor differentiation. After treatment, cell lysate was collected and analysed using immunoblot with appropriate antibody and results were quantified against β-actin. A, MCPIP induces autophagy characterized with the marker beclin-1 expression and ROS inhibitor or ER stress inhibitor inhibited MCPIP-induced expression of beclin-1. (*P<0.05). B, autophagy blocker 3'-MA blocked MCPIP-induced osteoclast-related gene TRAP and CTSK expression but not GRP78 (*P<0.05). C, autophagy blocker LY-294002 blocked MCPIP induced osteoclast-related gene TRAP and CTSK expression but not GRP78. (*P<0.05). D, blockage of autophagy by beclin-1 specific siRNA inhibited MCPIP-induced osteoclast-related gene TRAP and CTSK expression but not GRP78 both in protein and mRNA level. *P<0.05.

MCPIP-Induced Oxidative and ER Stress Leads to Autophagy Involved in OC Precursor Differentiation Increased expression of Beclin-1 is a commonly used marker of autophagy (Wang, 2008). Autophagy has been implicated in differentiation in some cellular contexts (Baerga et al., 2009; Singh et al., 2009). However, it was heretofore unclear whether autophagy has involvement in OC differentiation. Here it was found that forced expression of MCPIP increased expression of Beclin-1; this effect was suppressed by MCPIP siRNA, but not by non-specific scramble (Scr) siRNA (FIG. 5A, left panel and FIG. 10A). This result revealed that MCPIP induced autophagy in BMCs during differentiation into OC precursor cells.

ER stress is known to induce autophagy. To test whether MCPIP-induced ROS production and ER stress are involved directly in MCPIP-mediated autophagy, MCPIP-expressing cells were treated with $CeO_2$ nanoparticles that can trap free radicals, NADPH inhibitor apocynin, p47/AS, ER stress inhibitor TUDC, or IRE-1 siRNA. Immunoblot analysis showed that MCPIP-induced expression of Beclin-1 was inhibited significantly by inhibition of oxidative stress and ER stress and knockdown of genes involved in these stresses (FIG. 5A, right panel, and FIG. 10A). These results suggested that MCPIP-mediated autophagy was caused by oxidative stress and ER stress during differentiation of BMCs into OC precursor cells.

Recently, it has been shown that the PI3K inhibitors LY294002 and 3'-methyladenine (MA) stop the macroautophagic pathway at the sequestration step in rat hepatocytes (Blommaart et al., 1997; Petiot et al., 2000). In order to investigate whether autophagy is involved in MCPIP-mediated OC precursor differentiation, the effect of LY294002 and 3'-MA on expression of autophagy marker Beclin-1, lipidation of LC3 and expression of OC-related genes, TRAP and CTSK was tested. Real-time PCR analysis showed that 3'-MA and LY294002 significantly inhibited MCPIP-induced expression of Beclin-1, TRAP, and CTSK (FIG. 5D). Immunoblot assay demonstrated that 3'-MA and LY294002 inhibited the expression of Beclin-1, TRAP, and CTSK and lipidation of LC-3 (FIGS. 5B and C and Supplementary Figure S4B and C). However, no effect on expression of GRP78 induced by MCPIP was found revealing that inhibition of autophagy does not affect ER stress that is proposed to cause autophagy (FIGS. 5B and C and FIGS. 10B and C). Furthermore, upon inhibition of autophagy by knockdown of Beclin-1 with specific siRNA, MCPIP-induced expression of OC-related markers TRAP and CTSK was markedly suppressed, but scrambled siRNA showed little effects (FIG. 5E and FIG. 10D). The chemical inhibitors of autophagy and knockdown of Beclin-1 did not affect MCPIP-induced expression of GRP78, a marker of ER stress, which further leads to autophagy. These results strongly suggested that OC precursor cell differentiation induced by MCPIP expression is mediated via induction of ROS production that causes ER stress, which further leads to autophagy.

Figure 6:
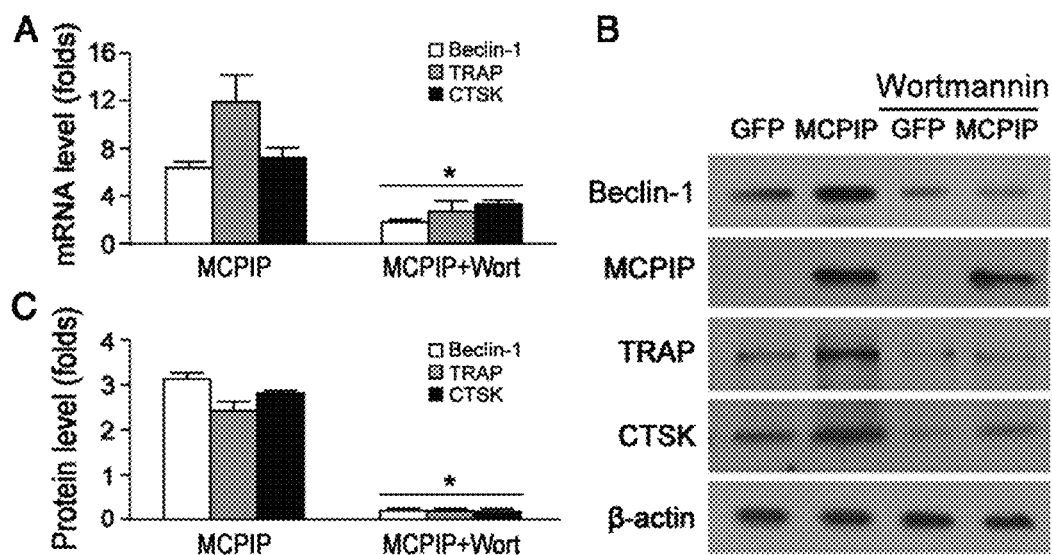
FIG. 6. MCPIP-induced OC precursor differentiation inhibited by PI3K inhibitor, wortmannin. (A) qRT-PCR showing induction of Beclin-1 and TRAP and CTSK at the transcript level by MCPIP transfection, and the inhibition effect of wortmannin on MCPIP. *P<0.05 versus MCPIP alone. (B) Immunoblotting show that MCPIP induced Beclin-1, and TRAP and CTSK, and that their induction was suppressed by wortmannin. (C) The intensities of immunoblots were measured and normalized to β-actin of the corresponding group. *P<0.05 compared with MCPIP alone.
Figure 11:
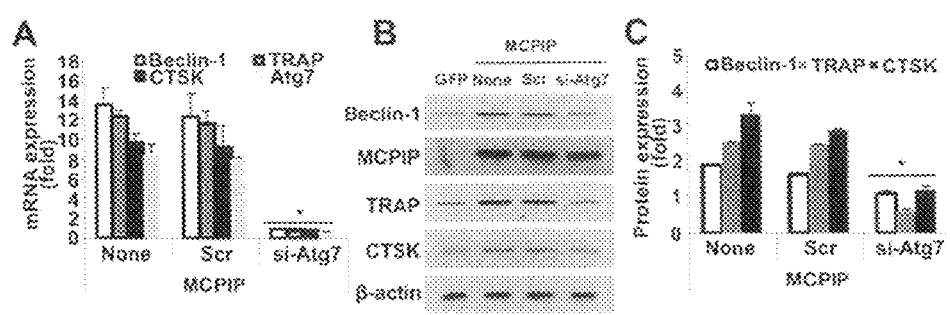
FIG. 11 MCPIP-induced autophagy marker Atg7 is necessary for induction of OC precursor differentiation. (A) qRT-PCR shows that transfection of MCPIP expression vector resulted in significantly increased mRNA levels of Atg7, Beclin-1, TRAP, and CTSK. Atg7-specific siRNA abolished MCPIP-induced expression of these genes. *P<0.05 compared with MCPIP alone. (B) Immunoblot shows that transfection with MCPIP expression vector caused induction of beclin-1, TRAP, and CTSK at the protein levels. Upregulation of these marker genes were inhibited by Atg7-specific siRNA but were not affected by scrambled siRNA. (C) The intensity of each protein was measured and normalized to β-actin of the corresponding group. *P<0.05 compared with MCPIP alone.

To further confirm the involvement of autophagy in OC precursor differentiation, a selective inhibitor of PI3K, wortmannin, was tested (Blommaart et al., 2007) on MCPIP-induced differentiation. Wortmannin severely inhibited MCPIP-induced OC precursor differentiation as indicated by the expression of OC markers at mRNA level by quantitative real-time PCR (qRT-PCR) and protein level by immunoblot analysis (FIG. 6A-C); inhibition of autophagy was reflected by changes in the Beclin-1 levels. In support of the involvement of autophagy in OC precursor differentiation, knockdown of Atg7 by specific siRNA severely inhibited expression of the OC markers TRAP and CTSK both at mRNA and protein level as measured by qRT-PCR and immunoblot analysis, respectively (FIGS. 11B and C), whereas scrambled siRNA did not significantly affect induction of these proteins.

Discussion for Examples 1-5:

The role of MCP-1 in differentiation of human bone marrow monocytes to OC precursors has been discovered for the first time herein. Furthermore, it has also been discovered herein that this process is mediated via the induction of MCPIP. MCP-1 induces the differentiation of monocytic cells into TRAP and CTSK-positive cells that do not express other OC functional markers such as αV integrin, β3 integrin, and MMP9 and do not exhibit bone resorption (Kim et al., 2006b). The differentiation into functional OCs requires RANKL in addition to MCP-1. Thus, the MCP-1 induced differentiation yields what might be considered osteoclastogenic cells or OC precursors.

It has been demonstrated that MCPIP mediates MCP-1-induced adipogenesis (Younce et al., 2009), glial differentiation of neuroprogenitor cells (Vrotsos et al., 2009), and angiogenesis (Niu et al., 2008). Here, it was found that forced expression of MCPIP resulted in high expression NADPH oxidase subunit $p47^{PHOX}$ and an increased level of membrane-associated $p47^{PHOX}$, causing ROS production. It is discovered herein that this oxidative stress causes ER stress that leads to autophagy involved in OC differentiation. The involvement of this sequence of processes in OC precursor differentiation is supported by the finding that inhibition of $p47^{PHOX}$ expression, NADPH oxidase activity, ROS production, ER stress, or autophagy by chemical inhibitors or by gene knockdown markedly suppressed MCPIP-induced expression of OC-related genes, TRAP and CTSK.

ROS are associated with multiple cellular functions such as cell proliferation, differentiation, and apoptosis (Wolf, 2005). Many reports revealed that high level of intracellular ROS also contributes to angiogenesis (Xia et al., 2007), epithelial-mesenchymal transition (Zhang et al., 2009), survival, and differentiation of OCs (Steinbeck et al., 1998; Yamasaki et al., 2009). The present results demonstrate that MCP-1 treatment and forced expression of MCPIP induce ROS generation during MCPIP-induced OC precursor differentiation. It has been reported that $CeO_2$ nanoparticles function as a free radical scavenger (Niu et al., 2007; Tsai et al., 2007; Younce and Kolattukudy, 2010). It has also been identified herein that $CeO_2$ inhibits the MCP-1- or MCPIP-induced ROS production and expression of OC-related genes.

NADPH oxidase is considered the most important source of ROS by respiratory burst in a monocyte/macrophage system (Decoursey and Ligeti, 2005; Bedard and Krause, 2007). NAD(P)H oxidase is a multiple subunit enzyme complex. Assembly of transmembrane subunits and cytosolic subunits of enzyme complex is the first important step for its activation. In this step, $p47^{PHOX}$ is the most important component which is phosphorylated, translocated from cytoplasm to the membrane to interact with $gp91^{phox}$ (Decoursey and Ligeti, 2005; Bedard and Krause 2007; Leto et al., 2009). Herein, it has been found that MCP-1 treatment or forced expression of MCPIP resulted in expression of $p47^{PHOX}$ and increased the membrane-associated $p47^{PHOX}$ level, and knockdown of MCPIP in MCP-1-treated cells decreased the expression and translocation of $p47^{PHOX}$. Moreover, NADPH oxidase activity inhibitor apocynin and knockdown of $p47^{PHOX}$ with antisense oligonucleotides inhibited membrane translocation of $p47^{PHOX}$, ROS production, and expression of OC-related genes CTSK and TRAP. Thus, MCPIP increases ROS production and induces expression of OC-related genes by increasing expression and translocation of $p47^{PHOX}$. As a zinc-finger protein with a nuclear localization sequence (Zhou et al., 2006) and RNase activity (Matsushita et al., 2009; Skalniak et al., 2009), MCPIP may serve as a novel regulator for several genes at the transcriptional and post-transcriptional level because of its DNA and RNA binding property. Therefore, MCPIP may regulate directly the expression of $p47^{PHOX}$ as a transcriptional factor. Secondly, it has been reported that MCPIP activates MAPK signal pathway (Younce and Kolattukudy, 2010). Activation of MAPK may be an important reason for the MCPIP-induced expression and translocation of $p47^{PHOX}$ oxidase.

ER stress results from the accumulation of misfolded proteins which leads to the induction of the unfolded protein response (UPR) (Malhotra and Kaufman, 2007). ROS production is known to cause proteins to aggregate and misfold. Here, it has been demonstrated that MCP-1 treatment and forced expression of MCPIP induced ER stress via generation of ROS in the monocytes during induction of OC differentiation. The important role of ER stress in monocyte differentiation into OC precursors was demonstrated by the findings that inhibition of ER stress inhibited differentiation and known ER stress inducers caused differentiation. ER stress inhibitor TUDC and knockdown of IRE-1 showed that inhibition of ER stress leads to inhibition of MCPIP-induced OC precursor differentiation. It has also been demonstrated herein that thapsgargin and tunicamycin that are known important inducers of UPR/ER stress induce differentiation of monocytes into OC precursors without MCP-1 or any other inducers. Thapsgargin, an inhibitor of ER-specific Ca-ATPase, has previously been shown to induce OC differentiation from RAW264.7 macrophage cells and mouse bone marrow cells (Takami et al., 1997; Yip et al., 2005).

Figure 12:
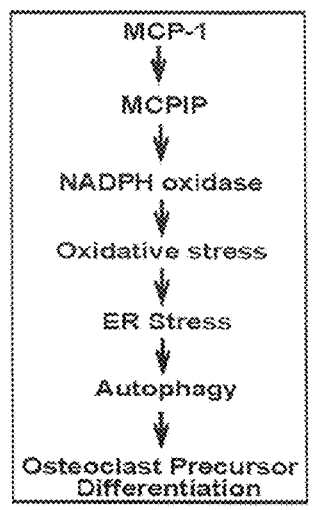
FIG. 12 Supplementary Scheme This figure shows a possible mechanism of how MCP-1 might effect Osteoclast precursor Differentiation

Autophagy is generally thought of as a survival mechanism, although its dysregulation has been linked to non-apoptotic cell death (Wang, 2008; Glick et al., 2010). Since differentiation involves disappearance of one set of proteins and appearance of a new set of proteins, a self-digestion process such as autophagy could be involved in this process. In fact, autophagy has been reported to be an important event for differentiation of the chronic myelogenous leukemia K562 cells (Colosetti et al., 2009), adipocytes (Malhotra and Kaufman, 2007; Singh et al., 2009; Goldman et al., 2010), paneth cells (Stappenbeck, 2010), and neuronal differentiation (Zeng and Zhou, 2008). Beclin-1 is a critical component in the class III PI3K complex (PI3KC3) that induces the formation of autophagosomes in mammalian systems (Wang, 2008). It has been demonstrated that Beclin-1 bridges autophagy and differentiation, and the process of autophagy and differentiation requires up-regulation of Beclin-1 (Wang, 2008). Inhibition of differentiation by PI3K inhibitors and knockdown of Beclin-1 and Atg7 strongly suggest that MCPIP induced OC precursor differentiation via autophagy. Emerging data now indicate that ER stress is a potent inducer of autophagy (Sakaki and Kaufman, 2008). Herein, the inventors have discovered that MCPIP induces OC precursor differentiation via autophagy which depends on MCPIP-induced ROS production and ER stress. It has been reported that ER stress can activate p38 MAPK signal pathway to induce autophagy (Kim et al., 2008). Moreover, ER stress activates phosphorylation of protein kinase-like ERK (PERK), an ER-localized transmembrane protein, and induction of IRE-1 is necessary for radiation-induced autophagy in mouse embryonic fibroblasts (Kim et al., 2010). Activation of NF-KB and MAPK signal pathway is necessary for OC differentiation (Huang et al., 2006). However, it was reported that MCPIP inhibits activation of NF-KB induced by IL-16 (Skalniak et al., 2009) and lipopolysaccharide stimulation (Liang et al., 2008) while over-expression of MCPIP can cause activation of JNK and p38 (Younce and Kolattukudy, 2010). Thus, activation of p38 instead of NF-κB signaling is probably involved in MCPIP-mediated differentiation of monocytes into OC precursors. The overall pathway involved in the MCP-1/MCPIP-mediated OC precursor differentiation is shown in FIG. 12.

Inflammatory bone erosion is involved in many pathological conditions (Lu et al., 2007; Ha et al., 2010). The novel inventive features recited herein provide a new insight into the mechanism by which MCP-1 induces differentiation of monocytic cells into TRAP- and CTSK-expressing cells that can proceed to differentiate into functional OCs in the presence of RANKL, and suggest that MCPIP is a novel target for therapy of inflammatory bone erosion.

Materials and Methods Related to Examples 1-5:

Reagents and Antibodies

Human BMCs were from Stemcell Technologies. α-MEM, FBS, HBSS, trypsin, recombinant human M-CSF (300-25), human MCP-1, and Trizol reagent were purchased from Invitrogen. Anti-β-actin, CTSK monoclonal antibodies, $CeO_2$ nanoparticles, apocynin, TUDC, 3'-MA, and LY294002 were from Sigma-Aldrich. Anti-TRAP, $p47^{PHOX}$, Fas, IRE-1, GRP78, Beclin-1, LC3 polyclonal antibodies, goat anti-rabbit and mouse secondary antibodies, and specific siRNA for IRE-1 and Beclin-1 were purchased from Santa Cruz Biotechnology. Specific siRNA for MCPIP and negative control siRNA were obtained from Ambion. Anti-MCPIP polyclonal antibody was prepared as indicated before (Zhou et al., 2006; Younce and Kolattukudy, 2010).

Cell Culture and Treatment

BMCs were cultured in α-MEM supplemented with 10% FBS containing 30 ng/ml M-CSF, 100 U/ml penicillin, and 100 μg/ml streptomycin in 5% $CO_2$ at 37° C. OC precursor cells were induced after 3-day culture as Ha et al. (2010). At this point, cells were treated with 50 ng/ml MCP-1, inhibitors, or gene transfection. For inhibitor treatment, $CeO_2$ (10 μM), apocynin (100 μg/ml), TUDC (100 μM), 3'-MA (50 μM), and LY294002 (20 μM) were added 6 h before gene transfection.

Gene Transfection and siRNA Knockdown

OC precursor cells were transfected with 1 μg GFP or MCPIP-GFP eukaryotic expression plasmids for gene-gain-function assay by using Fugene 6. For gene silencing, chemically synthesized siRNA duplex (100 nM) targeting MCPIP, IRE-1, or Beclin-1 was transfected into OC precursor cells using DharmaFECT (Dharmacon) for 24 h prior to transfection with MCPIP-GFP or GFP plasmid. A scrambled siRNA was used as a negative control. For knockdown expression of $p47^{PHOX}$, specific antisense (AS) (5'-CCA-GCAGGGCGATGTGACGGATGAA-3' (SEQ ID NO: 5)) and sense (5'-ATGGGGGACACCTTCATCCGTCAC-3' (SEQ ID NO: 6)) oligonucleotides were designed and synthesized by phosphorothioate modification by Integrated DNA Technologies. The oligonucleotides were transfected into OC precursor cells using Lipofectamine 2000 for 24 h before MCPIP-GFP plasmid transfection.

TRAP Staining

Three days after MCP-1 treatment or 4 days after MCPIP transfection, cells were fixed for histological staining for TRAP as described previously (Kim et al., 2006a). Briefly, following fixation, cells were stained with freshly prepared TRAP staining solution (naphthol AS-MX phosphate, fast red violet LB salt, and potassium sodium tartrate). On each coverslip, totally at least 500 cells were examined and the TRAP-positive cells were counted in 3-5 fields (20× objective), and the percentage of TRAP-positive cells was calculated.

Quantitative Real-Time Polymerase Chain Reaction

Cells were centrifuged after wash with PBS for twice. Cell pellet was resuspended in 1 ml Trizol reagent and the total RNA was extracted with chloroform and isopropanol, purified on Qiagen Mini-Prep column, and treated with DNase. High Capacity cDNA Reverse Transcription kit (Applied Biosystems) was used for cDNA preparation from 1 μg total RNA. qRT-PCR was done in triplicate in an ABI PRISM 7900HT Sequence Detection System with 5% cDNA product, primers (Supplementary Table S1) at 125 nM, and Fast SYBR Green Master Mix (Applied Biosystems). Relative quantitation of PCR products was done by the $2^{-\Delta\Delta CT}$ method, CT=cycles to threshold, and $\Delta\Delta CT$= (target gene CT)−(β-actin reference gene CT). Final data were described as fold changes against control cells.

ROS Production

Oxidant production in OC precursor cells was assessed by measuring the oxidation of intracellular DHR123 (Molecular Probes) as described previously (Younce et al., 2010). ROS production was expressed as folds compared with control cells expressing GFP alone.

Membrane Isolation

OC precursor cells were harvested, sonicated on ice in a buffer containing 100 mM KCl, 3 mM NaCl, 3.5 mM $MgCl_2$, 10 mM HEPES, 1 mM EGTA, 10 μg/ml pepstatin, 10 μg/ml leupeptin, and 0.5 mM PMSF; lysates were centrifuged at 600 g for 10 min at 4° C. to remove nuclei and unbroken cells. The supernatant was then ultracentrifuged at 100000 g for 1 h at 4° C. Membranes were washed in the same buffer, quantified (Lemarie), and resuspended in Laemmli sample buffer, before western blot analysis.

Sodium Dodecyl Sulfate-Polyacrylamide Gel Electrophoresis and Western Blotting

Sodium dodecyl sulfate-polyacrylamide gel electrophoresis (SDS-PAGE) and western blotting were performed as described elsewhere. Samples (30 μg of protein) were subjected to 12% SDS-PAGE for most of target protein and 18% SDS-PAGE for LC3-II and LC3, transferred onto PVDF membranes (Millipore), and assayed for MCPIP, $p47^{PHOX}$, TRAP, CTSK, GRP78, IRE-1, Beclin-1, LC3-II, and β-actin or Fas (loading control) protein expression by chemiluminescence detection (Pierce ECL kit) according to the manufacturer's instructions. The specific protein bands were quantified by densitometric analysis with GS-690 Image Densitometer (Bio-Rad).

Statistical Analysis

Data are represented as mean±SD of experiments performed on at least three separate occasions. Student's t-test was used to compare the means of normally distributed continuous variables. $P<0.05$ indicated statistical significance.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al., Eds., Cold Spring Harbor Laboratory Press, New York (1995); Arabidopsis, Meyerowitz et al, Eds., Cold Spring Harbor Laboratory Press, New York (1994) and the various references cited therein.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference in their entirety to the extent they are not inconsistent with the teachings herein.

REFERENCES

1. Azfer A., Niu J., Rogers L. M., et al. Activation of endoplasmic reticulum stress response during the development of ischemic heart disease. Am. J. Physiol. Heart Circ. Physiol. 2006; 291:H1411-H1420.
2, Baerga R., Zhang Y., Chen P. H., et al. Targeted deletion of autophagy-related 5 (atg5) impairs adipogenesis in a cellular model and in mice. Autophagy 2009; 5:1118-1130.
3. Bedard K., Krause K. H. The NOX family of ROS-generating NADPH oxidases: physiology and pathophysiology. Physiol. Rev. 2007; 87:245-313.
4. Blommaart E. F., Krause U., Schellens J. P. et al. The phosphatidylinositol 3-kinase inhibitors wortmannin and LY294002 inhibit autophagy in isolated rat hepatocytes. Eur. J. Biochem. 1997; 243:240-246.
5. Boyce B. F., Yao Z., Zhang Q., et al. New roles for osteoclasts in bone. Ann. NY Acad. Sci. 2007; 1116:245-254.
6. Colosetti P., Puissant A., Robert G., et al. Autophagy is an important event for megakaryocytic differentiation of the chronic myelogenous leukemia K562 cell line. Autophagy 2009; 5:1092-1098.
Decoursey T. E., Ligeti E. Regulation and termination of NADPH oxidase activity. Cell. Mol. Life. Sci. 2005; 62:2173-2193.
8. Gersten R. E., Friedrich E. B., Matsui T., et al. A role of phosphoinositide 3-kinase in monocyte recruitment under flow conditions. J. Biol. Chem. 2001; 276:26846-26851.
9. Glick D., Barth S., Macleod K. F. Autophagy: cellular and molecular mechanisms. J. Pathol. 2010; 221:3-12.
10, Goldman S., Mang Y., Jin S. Autophagy and adipogenesis: implications in obesity and type II diabetes. Autophagy 2010; 6:179-181.
11. Ha J., Choi H. S., Lee Y., et al. CXC chemokine ligand 2 induced by receptor activator of NF-kappa B ligand enhances osteoclastogenesis. J. Immunol. 2010; 184: 4717-4724.
12. Harris E. D. Jr. Rheumatoid arthritis: pathophysiology and implications for therapy. N. Engl. J. Med. 1990; 322:1277-1289.
13. Huang H., Ryu J., Ha J., et al. Osteoclast differentiation requires TAK1 and MKK6 for NFATc1 induction and NF-kappaB transactivation by RANKL. Cell Death Differ. 2006; 13:1879-1891.
14. Kim M. S., Day C. J., Morrison N. A. MCP-1 is induced by receptor activator of nuclear factor-κB ligand, promotes human osteoclast fusion, and rescues granulocyte macrophage colony-stimulating factor suppression of osteoclast formation. J. Biol. Chem. 2005; 280:16163-16169.
Kim M. S., Day C. J., Selinger C. I., et al. MCP-1-induced human osteoclast-like cells are tartrate-resistant acid phosphatase, NFATc1, and calcitonin receptor-positive but require receptor activator of NFkappaB ligand for bone resorption. J. Biol. Chem. 2006a; 281:1274-1285.
16. Kim M. S., Magno C. L., Day C. J., et al. Induction of chemokines and chemokine receptors CCR2b and CCR4 in authentic human osteoclasts differentiated with RANKL and osteoclast like cells differentiated by MCP-1 and RANTES. J. Cell. Biochem. 2006b; 97:512-518.
17. Kim D. S., Kim J. H., Lee G. H., et al. p38 mitogen-activated protein kinase is involved in endoplasmic reticulum stress-induced cell death and autophagy in human gingival fibroblasts. Biol. Pharm. Bull. 2008; 33:545-549.
18. Kim K. W., Moretti L., Mitchell L. R., et a. Endoplasmic reticulum stress mediates radiation-induced autophagy by perk-elF2alpha in caspase-3/7-deficient cells. Oncogene 2010; 29:3241-3251.
19. Kiviranta R., Morko J., Uusitalo H., et al. Accelerated turnover of metaphyseal trabecular bone in mice overexpressing cathepsin K. J. Bone Miner. Res. 2001; 16:1444-1452.
20. Leto T. L., Morand S., Hurt D., et al. Targeting and regulation of reactive oxygen species generation by Nox family NADPH oxidases. Antioxid. Redox Signal. 2009; 11:2607-2619.
21. Liang J., Wang J., Azfer A., et al. A novel CCCH-zinc finger protein family regulates proinflammatory activation of macrophages. J. Biol. Chem. 2008; 283:6337-6346.
Lu Y., Cai Z., Xiao G., et al. Monocyte chemotactic protein-1 mediates prostate cancer-induced bone resorption. Cancer Res. 2007; 67:3646-3653.
23. Malhotra J. D., Kaufman R. J. Endoplasmic reticulum stress and oxidative stress: a vicious cycle or a double-edged sword? Antioxid. Redox Signal. 2007; 9:2277-2293.
24, Malhotra J. D., Miao H., Zhang K., et al. Antioxidants reduce endoplasmic reticulum stress and improve protein secretion. Proc. Natl. Acad. Sci. USA 2008; 105:18525-18530.
25. Matsushita K, Takeuchi O., Standley D. M., et al. Zc3h12a is an RNase essential for controlling immune responses by regulating mRNA decay. Nature 2009; 458:1185-1190.
26. Miyamoto K., Ninomiya K., Sonoda K. H., et al. MCP-1 expressed by osteoclasts stimulates osteoclastogenesis in an autocrine/paracrine manner. Biochem. Biophys. Res. Commun. 2009; 383:373-377.
27. Mundy G. R. Osteoporosis and inflammation. Nutr. Rev. 2007; 65:S147-S151.
28. Niu J. Azfer A., Rogers L. M., et al. Cardioprotective effects of cerium oxide nanoparticles in a transgenic murine model of cardiomyopathy. Cardiovasc. Res. 2007; 73:549-559.
29. Niu J., Azfer A., Zhelyabovska O., et al. Monocyte chemotactic protein (MCP)-1 promotes angiogenesis via a novel transcription factor, MCP-1-induced protein (MCPIP). J. Biol. Chem. 2008; 283:14542-14551.
30. Petiot A., Ogier-Denis E., Blommaart E. F., et al. Distinct classes of phosphatidylinositol 3'-kinases are involved in signaling pathways that control macroautophagy in HT-29 cells. J. Biol. Chem. 2000; 275:992-998.
31. Sakaki K. Kaufman R. J. Regulation of ER stress-induced macroautophagy by protein kinase C. Autophagy 2008; 4:841-843.
32. Sakiyama H., Masuda R., Inoue N., et al. Establishment and characterization of macrophage-like cell lines expressing osteoclast-specific markers. J. Bone Miner. Metab. 2001; 19:220-227.
33. Sato K., Takayanagi H. Osteoclasts, rheumatoid arthritis, and osteoimmunology. Curr. Opin. Rheumatol. 2006; 18:419-426.
34. Singh R., Xiang Y., Wang Y., et al. Autophagy regulates adipose mass and differentiation in mice. J. Clin. Invest. 2009; 119:3329-3339.
35. Skalniak L, Mizgalska D., Zarebski A., et al. Regulatory feedback loop between NF-kappaB and MCP-1-induced protein 1 RNase. FEBS J. 2009; 276:5892-5905.
36. Stappenbeck T. S. The role of autophagy in Paneth cell differentiation and secretion. Mucosal. Immunol. 2010; 3:8-10.
37, Steinbeck M. J., Kim J. K., Trudeau M. J. Involvement of hydrogen peroxide in the differentiation of clonal HD-11EM cells into osteoclast-like cells. J. Cell. Physiol. 1998; 176:574-587.
38. Sugimura R., Li L. Shifting in balance between osteogenesis and adipogenesis substantially influences hematopoiesis. J. Mol. Cell. Biol. 2010; 2:61-62.
39, Takami M., Woo J. T., Takahashi N., et al. $Ca^{2+}$-ATPase inhibitors and $Ca^{2+}$-ionophore induce osteoclast-like cell formation in the cocultures of mouse bone marrow cells and calvarial cells. Biochem. Biophys. Res. Commun. 1997; 237:111-115.
40. Tsai Y. Y., Oca-Cossio J., Agering K., et al. Novel synthesis of cerium oxide nanoparticles for free radical scavenging. Nanomedicine (Lond) 2007; 2:325-332.
41. Vrotsos E. G., Kolattukudy P. E., Sugaya K. MCP-1 involvement in glial differentiation of neuroprogenitor cells through APP signaling. Brain Res. Bull. 2009; 79:97-103.
42. Wang J. Beclin 1 bridges autophagy, apoptosis and differentiation. Autophagy 2008; 4:947-948.
43. Wise G. E., Frazier-Bowers S., D'Souza R. N. Cellular, molecular, and genetic determinants of tooth eruption. Crit. Rev. Oral Biol. Med. 2002; 13:323-334.
44. Wolf G. Role of reactive oxygen species in angiotensin II-mediated renal growth, differentiation, and apoptosis. Antioxid. Redox Signal. 2005; 7:1337-1345.
45. Xia C., Meng Q., Liu L. Z., et al. Reactive oxygen species regulate angiogenesis and tumor growth through vascular endothelial growth factor. Cancer Res. 2007; 67:10823-10830.
46. Xue X., Piao J. H., Nakajima A., et al. Tumor necrosis factor alpha (TNFα) induces the unfolded protein response (UPR) in a reactive oxygen species (ROS)-dependent fashion, and the UPR counteracts ROS accumulation by TNFα. J. Biol. Chem. 2005; 280:33917-33925.
47. Yamasaki N., Tsuboi H., Hirao M., et al. High oxygen tension prolongs the survival of osteoclast precursors via macrophage colony-stimulating factor. Bone 2009; 44:71-79.
48, Yip K. H., Zheng M. H., Steer J. H., et al. Thapsigargin modulates osteoclastogenesis through the regulation of RANKL-induced signaling pathways and reactive oxygen species production. J. Bone Miner. Res. 2005; 20:1462-1471.
49. Younce C. W., Kolattukudy P. E. MCP-1 causes cardiomyoblast death via autophagy resulting from ER stress caused by oxidative stress generated by inducing a novel zinc-finger protein, MCPIP. Biochem. J. 2010; 426:43-53.
50. Younce C. W., Azfer A., Kolattukudy P. E. MCP-1 (monocyte chemotactic protein-1)-induced protein, a recently identified zinc finger protein, induces adipogenesis in 3T3-L1 pre-adipocytes without peroxisome proliferator-activated receptor gamma. J. Biol. Chem. 2009; 284:27620-27628.

51. Younce C. W., Wang K., Kolattukudy P. E. Hyperglycemia-induced cardiomyocyte death is mediated via MCP-1 production and induction of a novel zinc-finger protein MCPIP. Cardiovasc. Res. 2010; 87:665-674.

52. Zeng M., Zhou J. N. Roles of autophagy and mTOR signaling in neuronal differentiation of mouse neuroblastoma cells. Cell. Signal. 2008; 20:659-665.

53. Zhang K. H., Tian H. Y., Gao X., et al. Ferritin heavy chain-mediated iron homeostasis and subsequent increased reactive oxygen species production are essential for epithelial-mesenchymal transition. Cancer Res. 2009; 69:5340-5348.

54. Zhou L., Azter A., Niu J., et al. Monocyte chemoattractant protein-1 induces a novel transcription factor that causes cardiac myocyte apoptosis and ventricular dysfunction. Circ. Res. 2006; 98:1177-1185.

Supplementary Table S1 Primers for human genes tested in this study.

| Product | | Primer sequence |
|---|---|---|
| MCPIP | sense | 5'-GTTTCCAACGACACATACCGTGAC-3' (SEQ ID NO: 7) |
| | antisense | 5'-CTTCTTACG CAGGAAGTTGTCCAG-3' (SEQ ID NO: 8) |
| TRAP | sense | 5'-GCAGATCCTGGGTGCAGACTTC-3' (SEQ ID NO: 9) |
| | antisense | 5'-GGGAGCGGTCAGAGAATACGTGC-3' (SEQ ID NO: 10) |
| CTSK | sense | 5'-GAGGGGGCTACATGACCAATGC-3' (SEQ ID NO: 11) |
| | antisense | 5'-CTGCCTTGCCTGTTGGGTTGA-3' (SEQ ID NO: 12) |
| GRP78 | sense | 5'-ACAGCTTCTGATAATCAACCAA-3' (SEQ ID NO: 13) |
| | antisense | 5'-ACTTCAATCTGTGGGACCC-3' (SEQ ID NO: 14) |
| IRE-1 | sense | 5'-ACACCATCACCATGTACGACACCA-3' (SEQ ID NO: 15) |
| | antisense | 5'-ATTCAC TGTCCACAGTCACCACCA-3' (SEQ ID NO: 16) |
| IRE-1 | sense | 5'-ACACCATCACCATGTACGACACCA-3' (SEQ ID NO: 15) |
| | antisense | 5'-ATTCAC TGTCCACAGTCACCACCA-3' (SEQ ID NO: 16) |
| MMP9 | sense | 5'-TACCACCTCGAACTTTGACAGCGA-3' (SEQ ID NO: 17) |
| | antisense | 5'-GCCATTCACGTCGTCCTTATGCAA-3' (SEQ ID NO: 18) |
| αV integrin | sense | 5'-T TCCAAACTGGGAGCACAAGGAGA-3' (SEQ ID NO: 19) |
| | antisense | 5'-TGTAAGGCCACTGAAGATG GAGCA-3' (SEQ ID NO: 20) |
| β3 integrin | sense | 5'-CTCCTGTGTCCGCTACAAGGG-3' (SEQ ID NO: 21) |
| | antisense | 5'-GTCCAGTCGGAGTCACACAGG-3' (SEQ ID NO: 22) |
| beclin-1 | sense | 5'-CCGTGTCACCATCCAGGAACTC-3' (SEQ ID NO: 23) |
| | antisense | 5'-ACCATCCTGGCGAGGAGTTTC-3' (SEQ ID NO: 24) |
| Atg7 | sense | 5'-ATGTGGTGGCCCCAGGAGAT3' (SEQ ID NO: 25) |
| | antisense | 5'-AGATACCATCAATTCCACGG-3' (SEQ ID NO: 26) |
| β-actin | sense | 5'-GAGGCACTCTTCCAGCCTTCC-3' (SEQ ID NO: 27) |
| | antisense | 5'-GCGGATGTCCACGTCACACTT-3' (SEQ ID NO: 38) |

Scheme 1

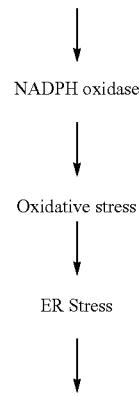

What is claimed is:

1. A method of treating a condition in a patient in need, the method comprising administering to the patient a therapeutically effective amount of a composition that inhibits the expression or action of MCPIP, wherein said condition comprises abnormal osteoclast-induced bone resorption, wherein the composition comprises siRNA specific for MCPIP, shRNA specific for MCPIP, or antisense nucleotide specific to an mRNA sequence encoding MCPIP.

2. The method of claim 1, wherein the patient in need is exhibiting pre-arthritic symptoms.

3. The method of claim 1, wherein the patient in need is exhibiting pre-osteoporotic symptoms.

4. The method of claim 1 wherein the composition comprises siRNA specific for MCPIP.

5. The method of claim 1 wherein the composition comprises an antisense nucleotide specific for MCPIP.

6. The method of claim 1 wherein the composition comprises shRNA specific for MCPIP.

7. The method of claim 1, wherein the composition is administered to the patient via intrabuccal, oral, rectal, pulmonary, ocular, or transdermal administration.

8. The method of claim 1, wherein the condition comprises an osteoporosis-related condition.

9. The method of claim 1, wherein the condition comprises Rheumatoid Arthritis.

10. The method of claim 1, wherein inhibiting MCPIP levels comprises directly administering the composition to the patient in need.

11. The method of claim 1, wherein administering the composition comprises administering a composition comprising a therapeutically effective amount of the composition that inhibits the expression or action of MCPIP and a pharmaceutically acceptable excipient.

12. A method of inhibiting osteoclast production in a patient in need, comprising:
    administering a therapeutically effective amount of a composition that inhibits the expression or action of MCPIP in the patient, wherein the composition comprises siRNA specific for MCPIP, shRNA specific for MCPIP, or an antisense nucleotide specific to an mRNA sequence encoding MCPIP.

13. The method of claim 12, wherein the patient in need is exhibiting symptoms of rheumatoid arthritis, osteoarthritis, and/or osteoporosis.

14. The method of claim 12, wherein administering a therapeutically effective amount of a composition includes a composition comprising: a composition that inhibits the expression or action of MCPIP, and a pharmaceutically acceptable excipient.

15. The method of claim 12, wherein the composition includes an MCPIP siRNA, an shRNA specific for MCPIP and/or an antisense nucleotide specific for MCPIP.

16. The method of claim 1, wherein the condition is an inflammatory joint disease.

17. A method of treating an inflammatory disease in a patient in need thereof, said method comprising:
    procuring human bone marrow mononuclear cells (BMCs) from said patient to obtain procured BMC's;
    treating said procured BMC's, ex vivo, by blocking expression of MCPIP in said cells to obtain treated BMC's, wherein the procured BMCs are treated with a composition comprising siRNA specific for MCPIP, shRNA specific for MCPIP, or an antisense nucleotide specific to an mRNA sequence encoding MCPIP;
    administering said treated BMC's to said patient.

18. The method of claim 17, wherein said treating comprises subjecting said procured BMC's to an antisense nucleotide specific to an mRNA sequence encoding MCPIP.

19. The method of claim 17, wherein said treating comprises subjecting said procured BMC's to siRNA specific to MCPIP.

20. The method of claim 17, wherein said inflammatory disease comprises osteoporosis, or arthritis.

* * * * *

SEQUENCE LISTING

<160> NUMBER OF SEQ ID NOS: 28

<210> SEQ ID NO 1
<211> LENGTH: 1800
<212> TYPE: DNA
<213> ORGANISM: Homo sapiens

<400> SEQUENCE: 1

| | | | | | | |
|---|---|---|---|---|---|---|
| atgagtggcc | cctgtggaga | gaagcctgtc | ctggaagcca | gccccaccat | gagtctgtgg | 60 |
| gaatttgagg | acagccacag | ccgtcagggc | accccaaggc | cgggtcaaga | gctggccgct | 120 |
| gaggaggcct | cggccctgga | actgcagatg | aaggtggact | tcttccggaa | gctgggctat | 180 |
| tcatccacgg | agatccacag | cgtcctgcag | aagctgggcg | tccaggcaga | caccaacacg | 240 |
| gtgctgggtg | agctggtgaa | acacgggaca | gccaccgagc | gggagcgcca | gacctcaccg | 300 |
| gaccctgcc | ctcagctccc | tctagtcccg | cggggtggtg | gcaccctaa | ggctcccaac | 360 |
| ctggagcctc | cactcccaga | agaggaaaag | gagggcagcg | acctgagacc | agtggtcatc | 420 |
| gatgggagca | acgtggccat | gagccatggg | aacaaggagg | tcttctcctg | ccggggcatc | 480 |
| ctgctggcag | tgaactggtt | tctggagcgg | ggccacacag | acatcacagt | gtttgtgcca | 540 |
| tcctggagga | aggagcagcc | tcggcccgac | gtgcccatca | cagaccagca | catcctgcgg | 600 |
| gaactggaga | agaagaagat | cctggtgttc | acaccatcac | gacgcgtggg | tggcaagcgg | 660 |
| gtggtgtgct | atgacgacag | attcattgtg | aagctggcct | acgagtctga | cgggatcgtg | 720 |
| gtttccaacg | acacataccg | tgacctccaa | ggcgagcggc | aggagtggaa | gcgcttcatc | 780 |
| gaggagcggc | tgctcatgta | ctccttcgtc | aatgacaagt | ttatgccccc | tgatgaccca | 840 |
| ctgggccggc | acgggcccag | cctggacaac | ttcctgcgta | agaagccact | cactttggag | 900 |
| cacaggaagc | agccgtgtcc | ctatggaagg | aaatgcacct | atgggatcaa | gtgccgattc | 960 |
| ttccacccag | agcggccaag | ctgccccag | cgctctgtgg | cagatgagct | ccgtgccaat | 1020 |
| gctctcctct | cacccccag | agcccaagc | aaggacaaaa | atggccggcg | gccttcacct | 1080 |
| tcatcccagt | ccagctctct | gctaacagag | agtgagcagt | gcagcctgga | tgggaagaag | 1140 |
| ctgggggccc | aggcatcccc | agggtcccgc | caagagggtc | taacacagac | ctatgcccca | 1200 |
| tcaggcagga | gcctcgcacc | tagcggggc | agtggcagca | gctttgggcc | cacagactgg | 1260 |
| ctcccacaga | cgctggactc | actcccgtac | gtctcccagg | attgcctgga | ctcgggcatt | 1320 |
| ggctccctgg | agagccagat | gtcggaactt | tgggggttc | gaggaggagg | ccctggtgag | 1380 |
| ccgggcccac | cccgagcccc | ttacacgggc | tacagtccct | atggatctga | gctcccagcc | 1440 |
| accgcagcct | tctctgcctt | tggccgggcc | atgggtgctg | gccacttcag | tgtccctgcc | 1500 |
| gactacccac | ccgcgcccc | tgcctttcca | cctcgagagt | actggtctga | accataccca | 1560 |
| ctgcccccac | ccacatcagt | ccttcaggag | ccccagtgc | agagcccagg | ggctggcagg | 1620 |
| agcccgtggg | gcagggcagg | cagcctggcc | aaggagcagg | ccagcgtgta | tactaagctg | 1680 |
| tgtggtgtgt | tccccccgca | cctggtggag | gctgtgatgg | ggcgcttccc | acagctcctg | 1740 |
| gacccccagc | agctggctgc | cgagatcctc | tcctacaagt | cccagcaccc | cagtgagtaa | 1800 |

<210> SEQ ID NO 2
<211> LENGTH: 599
<212> TYPE: PRT
<213> ORGANISM: Homo sapiens

<400> SEQUENCE: 2

-continued

```
Met Ser Gly Pro Cys Gly Glu Lys Pro Val Leu Glu Ala Ser Pro Thr
1               5                   10                  15
Met Ser Leu Trp Glu Phe Glu Asp Ser His Ser Arg Gln Gly Thr Pro
            20                  25                  30
Arg Pro Gly Gln Glu Leu Ala Ala Glu Glu Ala Ser Ala Leu Glu Leu
        35                  40                  45
Gln Met Lys Val Asp Phe Phe Arg Lys Leu Gly Tyr Ser Ser Thr Glu
    50                  55                  60
Ile His Ser Val Leu Gln Lys Leu Gly Val Gln Ala Asp Thr Asn Thr
65                  70                  75                  80
Val Leu Gly Glu Leu Val Lys His Gly Thr Ala Thr Glu Arg Glu Arg
                85                  90                  95
Gln Thr Ser Pro Asp Pro Cys Pro Gln Leu Pro Leu Val Pro Arg Gly
            100                 105                 110
Gly Gly Thr Pro Lys Ala Pro Asn Leu Glu Pro Pro Leu Pro Glu Glu
        115                 120                 125
Glu Lys Glu Gly Ser Asp Leu Arg Pro Val Val Ile Asp Gly Ser Asn
    130                 135                 140
Val Ala Met Ser His Gly Asn Lys Glu Val Phe Ser Cys Arg Gly Ile
145                 150                 155                 160
Leu Leu Ala Val Asn Trp Phe Leu Glu Arg Gly His Thr Asp Ile Thr
                165                 170                 175
Val Phe Val Pro Ser Trp Arg Lys Glu Gln Pro Arg Pro Asp Val Pro
            180                 185                 190
Ile Thr Asp Gln His Ile Leu Arg Glu Leu Lys Lys Lys Ile Leu
    195                 200                 205
Val Phe Thr Pro Ser Arg Arg Val Gly Gly Lys Arg Val Val Cys Tyr
210                 215                 220
Asp Asp Arg Phe Ile Val Lys Leu Ala Tyr Glu Ser Asp Gly Ile Val
225                 230                 235                 240
Val Ser Asn Asp Thr Tyr Arg Asp Leu Gln Gly Glu Arg Gln Glu Trp
                245                 250                 255
Lys Arg Phe Ile Glu Glu Arg Leu Leu Met Tyr Ser Phe Val Asn Asp
            260                 265                 270
Lys Phe Met Pro Pro Asp Asp Pro Leu Gly Arg His Gly Pro Ser Leu
    275                 280                 285
Asp Asn Phe Leu Arg Lys Lys Pro Leu Thr Leu Glu His Arg Lys Gln
    290                 295                 300
Pro Cys Pro Tyr Gly Arg Lys Cys Thr Tyr Gly Ile Lys Cys Arg Phe
305                 310                 315                 320
Phe His Pro Glu Arg Pro Ser Cys Pro Gln Arg Ser Val Ala Asp Glu
                325                 330                 335
Leu Arg Ala Asn Ala Leu Leu Ser Pro Pro Arg Ala Pro Ser Lys Asp
            340                 345                 350
Lys Asn Gly Arg Arg Pro Ser Pro Ser Ser Gln Ser Ser Ser Leu Leu
    355                 360                 365
Thr Glu Ser Glu Gln Cys Ser Leu Asp Gly Lys Lys Leu Gly Ala Gln
    370                 375                 380
Ala Ser Pro Gly Ser Arg Gln Glu Gly Leu Thr Gln Thr Tyr Ala Pro
385                 390                 395                 400
Ser Gly Arg Ser Leu Ala Pro Gly Gly Ser Gly Ser Phe Gly
                405                 410                 415
```

Pro Thr Asp Trp Leu Pro Gln Thr Leu Asp Ser Leu Pro Tyr Val Ser
            420                 425                 430
Gln Asp Cys Leu Asp Ser Gly Ile Gly Ser Leu Glu Ser Gln Met Ser
        435                 440                 445
Glu Leu Trp Gly Val Arg Gly Gly Pro Gly Glu Pro Gly Pro Pro
    450                 455                 460
Arg Ala Pro Tyr Thr Gly Tyr Ser Pro Tyr Gly Ser Glu Leu Pro Ala
465                 470                 475                 480
Thr Ala Ala Phe Ser Ala Phe Gly Arg Ala Met Gly Ala Gly His Phe
            485                 490                 495
Ser Val Pro Ala Asp Tyr Pro Pro Ala Pro Ala Phe Pro Pro Arg
        500                 505                 510
Glu Tyr Trp Ser Glu Pro Tyr Pro Leu Pro Pro Thr Ser Val Leu
    515                 520                 525
Gln Glu Pro Pro Val Gln Ser Pro Gly Ala Gly Arg Ser Pro Trp Gly
530                 535                 540
Arg Ala Gly Ser Leu Ala Lys Glu Gln Ala Ser Val Tyr Thr Lys Leu
545                 550                 555                 560
Cys Gly Val Phe Pro Pro His Leu Val Glu Ala Val Met Gly Arg Phe
            565                 570                 575
Pro Gln Leu Leu Asp Pro Gln Gln Leu Ala Ala Glu Ile Leu Ser Tyr
        580                 585                 590
Lys Ser Gln His Pro Ser Glu
        595

<210> SEQ ID NO 3
<211> LENGTH: 1791
<212> TYPE: DNA
<213> ORGANISM: Mus musculus

<400> SEQUENCE: 3
atgagtgacc cttgtggaac gaagcctgtc caagaatcca accccaccat gagtctgtgg     60
agtcttgagg acagacacag cagccagggt cgacctcagc cagaccagga tcctgtggct    120
aaagaggccc ctacttccga gctgcagatg aaggtggact ttttccgtaa actgggtac    180
tcgtcctctg agatccacag tgtcctgcag aagctgggag tccaagcaga caccaacacg    240
gtgctagggg aattggtgaa gcatggctca gctactgaac gagaatgcca ggccctgacg    300
gccccccagcc cccagccccc tctggtgccc cggggtggaa gcaccccaa gccttccact    360
ctagaaccct cactcccaga ggaggacaga gagggcagcg acctgagacc tgtggtcatc    420
gacggaagca atgtggccat gagccatggg aacaaggaag tcttctcttg ccggggcatt    480
ctgctggctg tgaactggtt tctggagcga ggccacacag atattaccgt gtttgtgcca    540
tcttggagga aggaacagcc tcgaccagat gtgcctatca cagaccagca catccttcgg    600
gaactagaga aaaagaagat cttggtgttc acgccatcca ggcgggtcgg cggcaagcgc    660
gtggtgtgct atgatgaccg cttcattgtg aagctgcct tcgaatccga cggagtggtg    720
gtctccaatg acacgtaccg agacctccaa ggcgagaggc aggagtggaa acgcttcatc    780
gaggagcggc tgctcatgta ctccttcgtc aatgacaagt tcatgccccc tgacgaccct    840
ttaggacggc atgggcctag cctggacaac ttccttcgta gaaaccact gccttctgag    900
cacaggaagc agccatgccc ctatgggaag aaatgtacgt atgaaatcaa gtgccgattt    960
ttccaccctg agcggccaag ccgtcccag cgctctgtgg ccgatgagct ccgtgccaac   1020
gctctcctct cacctcccag gactccagtc aaggacaaaa gtagccagag gccttcccct   1080

```
gcctctcagt ccagctctgt gtccctagag gctgaaccag gcagcctgga tgggaaaaag    1140
ctgggtgcca ggtcatctcc gggtccccac cgagaaggct caccgcagac ctgtgctcca    1200
gctggcagga gcctccctgt tagtgggggc agctttgggc ccacagagtg gcttgcacac    1260
acccaggact cactcccata cacctcccag gagtgccttg attcaggcat tggttccctg    1320
gagagccaga tgtcagaatt atggggcgtg cgaggaggca gccctgggga gtcgggcccc    1380
actcggggcc cctatgcagg ttatcacagc tatggatcca aggtcccagc agcaccttcc    1440
ttttctcctt ttagaccagc catgggtgct ggccacttca gtgtccccac cgactatgtg    1500
cccccgccac ccacctaccc atccagagag tactggtctg agccgtaccc attaccccca    1560
cccactcctg tccttcagga gccccagaga cccagccccg gggctggtgg gggcccctgg    1620
ggcagggtgg gtgacctggc caaagaaagg gctggtgtat ataccaagct gtgtggtgtc    1680
ttccccccac acctggtaga agctgtaatg agacgcttcc cacagctgct ggatccgcag    1740
cagctggccg cagagatcct gtcttacaag tcccagcacc tcagtgagta a             1791
```

<210> SEQ ID NO 4
<211> LENGTH: 596
<212> TYPE: PRT
<213> ORGANISM: Mus musculus

<400> SEQUENCE: 4

```
Met Ser Asp Pro Cys Gly Thr Lys Pro Val Gln Glu Ser Asn Pro Thr
1               5                   10                  15

Met Ser Leu Trp Ser Leu Glu Asp Arg His Ser Ser Gln Gly Arg Pro
            20                  25                  30

Gln Pro Asp Gln Asp Pro Val Ala Lys Glu Ala Pro Thr Ser Glu Leu
        35                  40                  45

Gln Met Lys Val Asp Phe Phe Arg Lys Leu Gly Tyr Ser Ser Ser Glu
    50                  55                  60

Ile His Ser Val Leu Gln Lys Leu Gly Val Gln Ala Asp Thr Asn Thr
65                  70                  75                  80

Val Leu Gly Glu Leu Val Lys His Gly Ser Ala Thr Glu Arg Glu Cys
                85                  90                  95

Gln Ala Leu Thr Ala Pro Ser Pro Gln Pro Pro Leu Val Pro Arg Gly
            100                 105                 110

Gly Ser Thr Pro Lys Pro Ser Thr Leu Glu Pro Ser Leu Pro Glu Glu
        115                 120                 125

Asp Arg Glu Gly Ser Asp Leu Arg Pro Val Val Ile Asp Gly Ser Asn
    130                 135                 140

Val Ala Met Ser His Gly Asn Lys Glu Val Phe Ser Cys Arg Gly Ile
145                 150                 155                 160

Leu Leu Ala Val Asn Trp Phe Leu Glu Arg Gly His Thr Asp Ile Thr
                165                 170                 175

Val Phe Val Pro Ser Trp Arg Lys Glu Gln Pro Arg Pro Asp Val Pro
            180                 185                 190

Ile Thr Asp Gln His Ile Leu Arg Glu Leu Glu Lys Lys Lys Ile Leu
        195                 200                 205

Val Phe Thr Pro Ser Arg Arg Val Gly Gly Lys Arg Val Val Cys Tyr
    210                 215                 220

Asp Asp Arg Phe Ile Val Lys Leu Ala Phe Glu Ser Asp Gly Val Val
225                 230                 235                 240
```

Val Ser Asn Asp Thr Tyr Arg Asp Leu Gln Gly Glu Arg Gln Glu Trp
                245                 250                 255

Lys Arg Phe Ile Glu Glu Arg Leu Leu Met Tyr Ser Phe Val Asn Asp
            260                 265                 270

Lys Phe Met Pro Pro Asp Asp Pro Leu Gly Arg His Gly Pro Ser Leu
        275                 280                 285

Asp Asn Phe Leu Arg Lys Lys Pro Leu Pro Ser Glu His Arg Lys Gln
    290                 295                 300

Pro Cys Pro Tyr Gly Lys Lys Cys Thr Tyr Glu Ile Lys Cys Arg Phe
305                 310                 315                 320

Phe His Pro Glu Arg Pro Ser Arg Pro Gln Arg Ser Val Ala Asp Glu
                325                 330                 335

Leu Arg Ala Asn Ala Leu Leu Ser Pro Pro Arg Thr Pro Val Lys Asp
            340                 345                 350

Lys Ser Ser Gln Arg Pro Ser Pro Ala Ser Gln Ser Ser Ser Val Ser
        355                 360                 365

Leu Glu Ala Glu Pro Gly Ser Leu Asp Gly Lys Lys Leu Gly Ala Arg
    370                 375                 380

Ser Ser Pro Gly Pro His Arg Glu Gly Ser Pro Gln Thr Cys Ala Pro
385                 390                 395                 400

Ala Gly Arg Ser Leu Pro Val Ser Gly Gly Ser Phe Gly Pro Thr Glu
                405                 410                 415

Trp Leu Ala His Thr Gln Asp Ser Leu Pro Tyr Thr Ser Gln Glu Cys
            420                 425                 430

Leu Asp Ser Gly Ile Gly Ser Leu Glu Ser Gln Met Ser Glu Leu Trp
        435                 440                 445

Gly Val Arg Gly Gly Ser Pro Gly Glu Ser Gly Pro Thr Arg Gly Pro
    450                 455                 460

Tyr Ala Gly Tyr His Ser Tyr Gly Ser Lys Val Pro Ala Ala Pro Ser
465                 470                 475                 480

Phe Ser Pro Phe Arg Pro Ala Met Gly Ala Gly His Phe Ser Val Pro
                485                 490                 495

Thr Asp Tyr Val Pro Pro Pro Thr Tyr Pro Ser Arg Glu Tyr Trp
            500                 505                 510

Ser Glu Pro Tyr Pro Leu Pro Pro Thr Pro Val Leu Gln Glu Pro
        515                 520                 525

Gln Arg Pro Ser Pro Gly Ala Gly Gly Pro Trp Gly Arg Val Gly
    530                 535                 540

Asp Leu Ala Lys Glu Arg Ala Gly Val Tyr Thr Lys Leu Cys Gly Val
545                 550                 555                 560

Phe Pro Pro His Leu Val Glu Ala Val Met Arg Arg Phe Pro Gln Leu
                565                 570                 575

Leu Asp Pro Gln Gln Leu Ala Ala Glu Ile Leu Ser Tyr Lys Ser Gln
            580                 585                 590

His Leu Ser Glu
        595

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccagcagggc gatgtgacgg atgaa                                                25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgggggaca ccttcatccg tcac                                                 24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtttccaacg acacataccg tgac                                                 24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttcttacgc aggaagttgt ccag                                                 24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcagatcctg ggtgcagact tc                                                   22

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggagcggtc agagaatacg tgc                                                  23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11 gaggggggcta catgaccaat gc                                              22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgccttgcc tgttgggttg a                                                21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acagcttctg ataatcaacc aa                                               22

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acttcaatct gtgggaccc                                                   19

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acaccatcac catgtacgac acca                                             24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
attcactgtc cacagtcacc acca                                             24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
taccacctcg aactttgaca gcga                                             24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gccattcacg tcgtccttat gcaa                                            24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttccaaactg ggagcacaag gaga                                            24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgtaaggcca ctgaagatgg agca                                            24

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctcctgtgtc cgctacaagg g                                               21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtccagtcgg agtcacacag g                                               21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccgtgtcacc atccaggaac tc                                              22

```
-continued

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
accatcctgg cgaggagttt c                                              21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgtggtggc cccaggagat                                                20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agataccatc aattccacgg                                                20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaggcactct tccagccttc c                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcggatgtcc acgtcacact t                                              21
```